United States Patent [19]

Yabuta et al.

[11] Patent Number: 6,037,145

[45] Date of Patent: *Mar. 14, 2000

[54] PROCESS FOR PRODUCTION OF PROTEIN

[75] Inventors: Masayuki Yabuta, Tatebayashi; Kazuhiro Ohsuye, Ohta, both of Japan

[73] Assignee: Suntory Limited, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/523,373

[22] Filed: Sep. 5, 1995

[30] Foreign Application Priority Data

Sep. 7, 1994 [JP] Japan .................................. 6-238595
Nov. 7, 1994 [JP] Japan .................................. 6-296028

[51] Int. Cl.⁷ ............................. C12N 15/63; C12N 1/21; C12N 9/52

[52] U.S. Cl. ..................... 435/69.1; 435/69.7; 435/194; 435/207; 435/219; 435/220; 435/224; 435/252.3; 435/252.33; 435/254.11; 530/326

[58] Field of Search .................................. 435/69.7, 194, 435/207, 219, 220, 224, 814, 69.1, 252.3, 254.11, 252.33; 530/326

[56] References Cited

U.S. PATENT DOCUMENTS

| | | | |
|---|---|---|---|
| 5,013,653 | 5/1991 | Huston et al. | 435/69.7 |
| 5,077,204 | 12/1991 | Brake et al. | 435/68.1 |
| 5,116,750 | 5/1992 | Gelfand et al. | 435/193 |
| 5,506,120 | 4/1996 | Yamamoto et al. | 435/69.7 |

FOREIGN PATENT DOCUMENTS

| | | |
|---|---|---|
| 0 114 506 | 8/1984 | European Pat. Off. |
| 0528686A2 | 2/1993 | European Pat. Off. |

OTHER PUBLICATIONS

Clements et al., *Gene*, 106:267–72 (1991).

M.P. Broekhuijsen, *Jourrnal of Biotechnology*, 31:135–45 (1993).

Carmona et al, "Nucleotide Sequence of the Serine Protease Gene of *Staphylococcus aureus*, Strain V8", *Nucleic Acids Research*, 15(16):6757 (1987).

Houmard et al, "Staphylococcal Protease: A Proteolytic Enzyme Specific for Glutamoyl Bonds", *Proc. Nat. Acad. Sci.*, 69(12):3506–3509 (1972).

Jayaswal et al, "Cloning and Expression of a *Staphylococcus aureus* Gene Encoding a Peptidoglycan Hydrolase Activity", *Journal of Bacteriology*, 172(10):5783–5788 (1990).

Sugimura et al, "Purification, Characterization, and Primary Structure of *Escherichia coli* Protease VII with Specificity for Paired Basic Residues: Identity of Protease VII and OmpT", *Journal of Bacteriology*, 170(12):5625–5632 (1988).

Sugimura, "Mutant Isolation and Cloning of the Gene Encoding Protease VII from *Escherichia coli*", *Biochemical and Biophysical Research Communications*, 153(2):753–759 (1988).

Vieira et al, "The pUC Plasmids, an M13mp7–Derived System for Insertion Mutagenesis and Sequencing with Synthetic Universal Primers", *Gene*, 19:259–268 (1982).

Taylor et al, "A Correction in the Nucleotide Sequence of the Tn903 Kanamycin Resistance Determinant in pUC4K", *Nucleic Acids Research*, 16(1):358 (1988).

Yoshikawa et al, "Recombinant Human Glucagon: Large–Scale Purification and Biochemical Characterization", *Journal of Protein Chemistry*, 11(5):517–525 (1992).

Yabuta et al., "Hyperproduction of a Recombinant Fusion Protein of *Staphylococcus aureus* V8 Protease to Release an Active V8 Protease Derivative," *Applied Microbiology and Biotechnology*, vol. 44, 1995, pp. 118–125.

Seeboth et al., "In–Vitro Cleavage of a Fusion Protein Bound to Cellulose using the Soluble ysc $F_s$ (Kex2) variant," *Applied Microbiology and Biotechnology*, vol. 37, 1992, pp. 621–625.

Suominen et al., "Enhanced Recovery and Purification of Aspergillus Glucoamylase from *Saccharomyces Cerevisiae* by the Addition of Poly(aspartic acid) Tails," *Enzyme Microb. Technol.*, vol. 15, 1993, pp. 593–600.

Van Den Bergh et al., "Secretion of Biologically Active Porcine Prophospholipase $A_2$ by *Saccharomyces Cerevisiae*," *European Journal of Biochemistry*, vol. 170, 1987, pp. 241–246.

Contreras et al., "Efficient KEX2–like Processing of a Glucoamylase–Interleukin–6 Fusion Protein by *Aspergillus Nidulans* and Secretion of Mature Interleukin–6," *Biotechnology*, vol. 9, 1991, pp. 378–381.

Hanke et al., "Processing by OmpT of Fusion Proteins Carrying the H1y A transport signal during secretion by the *Eschereichia Coli* hemolysin Transport System," *Mol. Gen. Genet.*, vol. 233, 1992, pp. 42–48.

Lennick et al. High–level expression of α–human atrial natriuretic peptide from multiple joined genes in *Escherichia coli*. Gene. vol. 61, No. 1, pp. 103–112, 1987.

White et al. A novel activity of OmpT: proteolysis under extreme denaturing conditions. The Journal of Biological Chemistry. vol. 270, No. 22, pp. 12990–12994, Jun. 2, 1995.

*Primary Examiner*—Elizabeth C. Kemmerer
*Assistant Examiner*—Brian Lathrop
*Attorney, Agent, or Firm*—Burns, Doane, Swecker & Mathis, L.L.P.

[57] ABSTRACT

A process for the production of a desired polypeptide comprising the steps of: (1) transforming host cells with an expression vector comprising a gene coding for a fusion protein comprising a desired polypeptide and a protective polypeptide; (2) culturing the transformed host cells so as to express said gene to produce a fusion protein; and (3) excising the desired polypeptide from the fusion protein with a protease intrinsic to the host cells. According to the present invention, a large amount of a desired polypeptide can be produced at a low cost. Especially according to the present invention, a large amount of *S. aureus* V8 protease can be efficiently produced at low cost using a safe host such as *E. coli* according to gene recombination procedures.

34 Claims, 16 Drawing Sheets

PRIMER I ; 5' ACCGCTCGAGGTTATATTACCAAATAACGAT 3' (SEQ ID NO:2)

PRIMER II ; 5' CTTAATGTCGACTTAAGCTGCATCTGGATT 3', (SEQ ID NO:3)

PRIMER III; 5' TCGCGTCGACTTATTGGTCATCGTTGGCAAA 3, (SEQ ID NO:4)

Fig.4(a)

```
1
MTMITDSLAVVLQRRDWENPGVTQLNRLAAHPPFASWRNSDDARTDRPSQ  50
QLRSLNGEWRFAWFPAPEAVPDSLLDSDLPEADTVVPSNWQMHGYDAEL  100
RLYRRHHRWGRSGSPLRAHEQFLEVILPNNDRHQITDTTNGHYAPVTYIQ  150
VEAPTGTFIASGVVGKDTLLTNKHVVDATHGDPHALKAFPSAINQDNYP  200
NGGFTAENITKYSGEGDLAIVKFSPNEQNKHIGEVVKPATMSNNAETQVN  250
QNITVTGYPGDKPVATMWESKGKITYLKGEAMQYDLSTTGGNSGSPVFNE  300
KNEVIGIHWGGVPNEFNGAVFINENVRNFLKQNIEDIHFANDDQ (SEQ ID NO:5)
                                          344
```

AMINO ACID SEQUENCE OF FUSION PROTEIN ENCODED IN pV8RPT (-)
(V8 PROTEASE REGION IS UNDERLINED)

Fig.4(b)

```
1
MTMITDSLAVVLQRRDWENPGVTQLNRLAAHPPFASWRNSDDARTDRPSQ    50
QLRSLNGEWRFAWFPAPEAVPDSLLDSDLPEADTVVVPSNWQMHGYDAEL    100
RLYRRHHRWGRSGSPLRAHEQFLEVILPNNDRHQITDTTNGHYAPVTYIQ    150
VEAPTGTFIASGVVVGKDTLLTNKHVVDATHGDPHALKAFPSAINQDNYP    200
NGGFTAENITKYSGEGDLAIVKFSPNEQNKHTGEVVKPATMSNNAETQVN    250
QNITVTGYPGDKPVATMWESKGKITYLKGEAMQYDLSTTGGNSGSPVFNE    300
KNEVIGIHWGGVPNEFNGAVFINENVRNFLKQNIEDIHFANDDQPNNPDN    350
PDNPNNPDNPNNPDEPNNPDNPNNPDNPDNGDNNNSDNPDAA    392
```

(SEQ ID NO:6)

AMINO ACID SEQUENCE OF FUSION PROTEIN ENCODED IN pV8RPT (+)
(V8 PROTEASE REGION IS UNDERLINED)

Fig. 6

```
  1
  MTMITDSLAVVLQRRDWENPGVTQLNRLAAHPPFASWRNSDDARTDRPSQ    50
  QLRSLNGEWRFAWFPAPEAVPDSLLDSDLPEADTVVVPSNWQMHGYDAEL   100
       →
  RLYRRHHRWGRSGSPLRAHEQFLEVILPNNDRHQITDTTNGHYAPVTYIQ   150
  VEAPTGTFIASGVVVGKDTLLTNKHVVDATHGDPHALKAFPSAINQDNYP   200
  NGGFTAENITKYSGEGDLAIVKFSPNEQNKHIGEVVKPATMSNNAETQVN   250
  QNITVTGYPGDKPVATMWESKGKITYLKGEAMQYDLSTTGGNSGSPVFNE   300
  KNEVIGIHWGGVPNEFNGAVFINENVRNFLKQNIEDRLYRRHHRWGRSGS   350
  PLRAHEQFLECGNGKTAFQVLEEYPDSGENIVDALAVFLRRLHSIPVCNC   400
  PFNSDRVFRLAQAQSRMNNGLVDASFDDERNGWPVEQVWKEMHKLLPFS    450
  PDSVVTHGDFSLDNLIFDEGKLIGCIDVGRVGIADRYQDLAILWNCLGEF   500
  SPSLQKRLFQKYGIDNPDMNKLQFHLMLDEFF  (SEQ ID NO:7)      532
```

AMINO ACID SEQUENCE OF FUSION PROTEIN ENCODED IN pV8D
V8 PROTEASE REGION IS UNDERLINED
→ CLEAVAGE SITE FOR OmpT PROTEASE

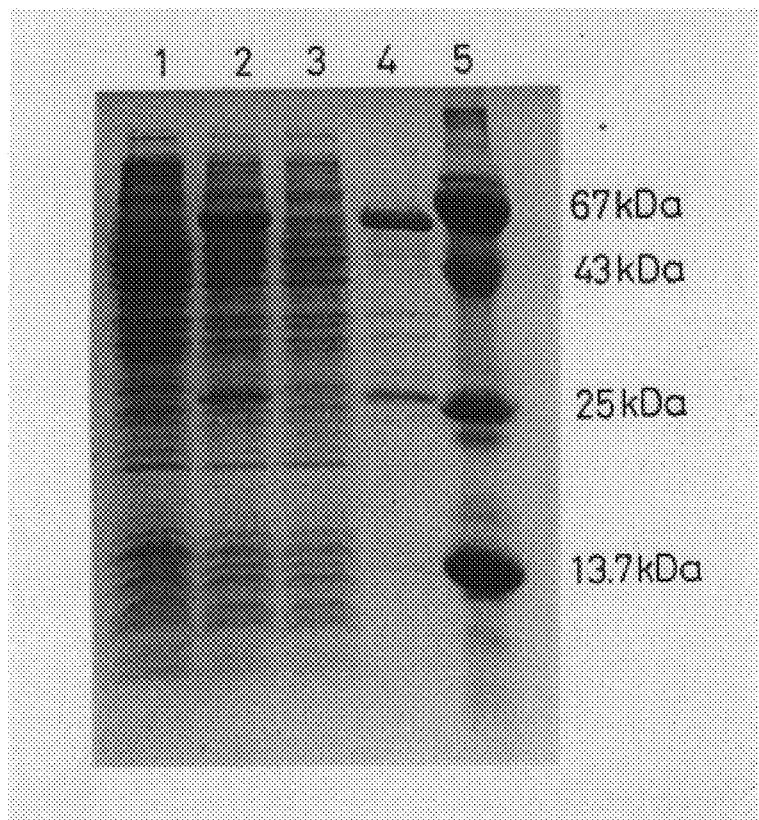

INCLUSION BODIES DERIVED FROM E.coli JM101

INCLUSION BODIES DERIVED FROM E.coli W3110M25 (ompT)

PROCESSING OF V8D FUSION PROTEIN BY ompT PROTEASE
1. MOLECULAR WEIGHT MARKER
2. IMEDIATEHS AFTER SOLUBILIZATION WITH UREA
3. AFTER 2 HOURS

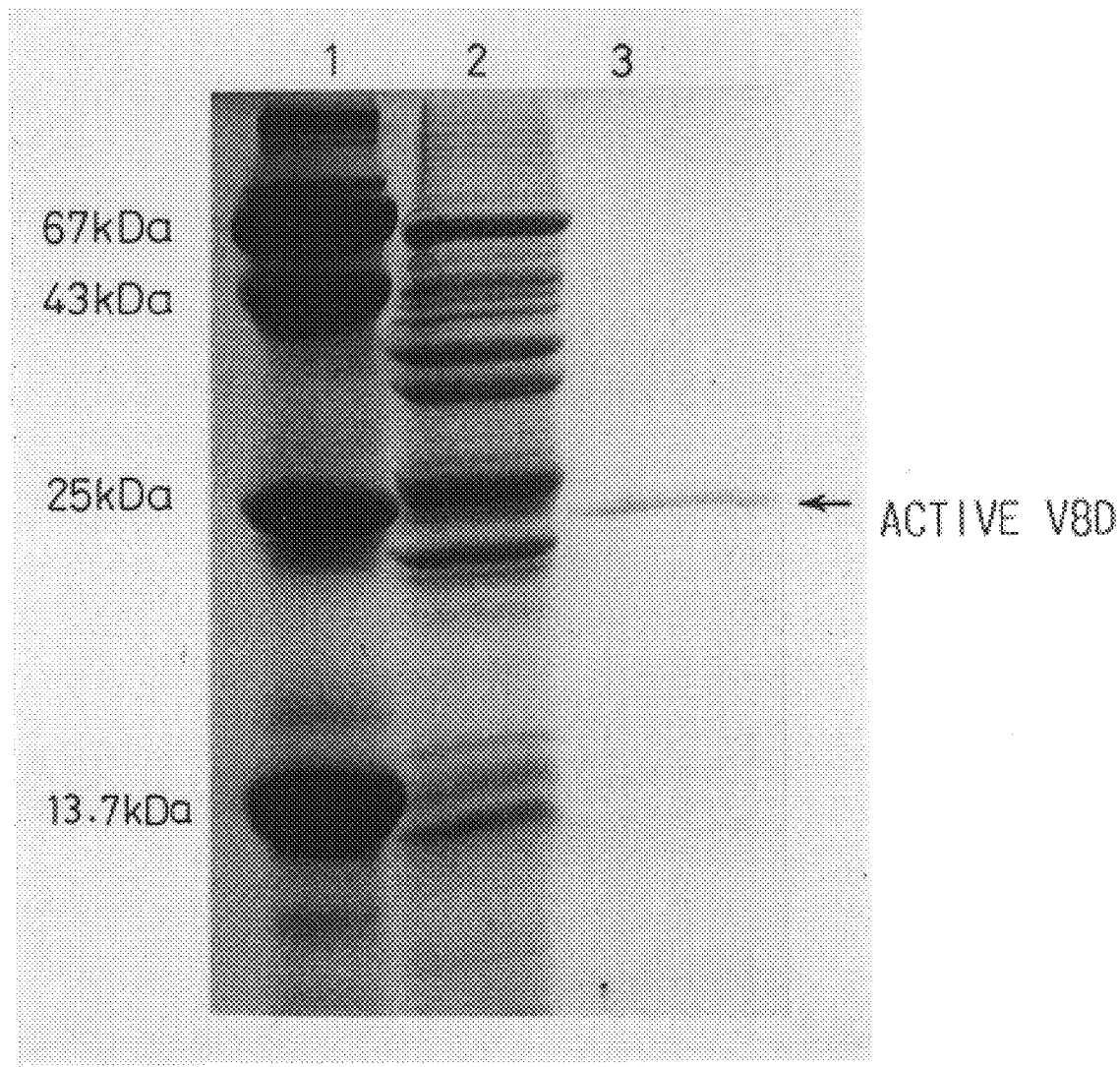

RECOMBINANT V8 PROTEASE

S. aureus V8 PROTEASE

PEAK1. hCT[G]
PEAK2. FUSION PROTEIN OF HUMAN CALCITONIN
PRECURSOR (hCT[G])
PEAK3. β-GALACTOSIDASE DERIVATIVE

Fig. 11

PRIMER a; 5' ATCGTTGGCCATATGGATATCTTCAATATT (SEQ ID NO:8)
                         NdeI

PRIMER b; 5' GACTTATTGGTCATCGAGCTCAAAAATGGATATC (SEQ ID NO:9)
                              SacI

PRIMER c; 5' GACTTATTGGTCGAGCTCGGCAAAATGGAT (SEQ ID NO:10)
                         SacI

PRIMER d; 5' ATCTGGGTTGAGCTCATCGTTGGCAAAATGGAT (SEQ ID NO:11)
                        SacI

PRIMER e; 5' ATCTGGTTGGAGCTCTTGGTCATCGTTGGCAAA (SEQ ID NO:12)
                        SacI

PRIMER f; 5' ACAAAATCATATGGAACGCCTATATCGCCGACAT (SEQ ID NO:13)
                     NdeI

PRIMER g; 5' AATATTGAAGAGCTCCGCCTATATCGCCGACAT (SEQ ID NO:14)
                         SacI

PRIMER h; 5' GAATGGCAAAAGCTTATGCATTCTTT (SEQ ID NO:15)
                              EcoT22I

PRIMERS a~e: CORRESPONDING TO V8 PROTEASE GENE
PRIMERS f, g: CORRESPONDING TO R6 SEQUENCE GENE
PRIMER h: CORRESPONDING TO AMINOGLUCOSIDE 3'-
          PHOSPHOTRANSFERSE tAPT; TRUNCATED AMINOGLYCOSIDE 3'-PHOSPHOTRANSFERAS

Fig. 13

| PLASMID | C-TERMINAL SEQUENCE OF V8 PROTEASE REGION | INCLUSION BODIES FORMATION | |
|---|---|---|---|
| pV8D | ---[NIED]-RLYRRHHR----- (209) | + | (SEQ ID NO:16) |
| pV8H | ---[NIEDIH]-MERLYRRHHR----- | + | (SEQ ID NO:17) |
| pV8F | ---[NIEDIHF]-ELRLYRRHHR----- | + | (SEQ ID NO:18) |
| pV8A | ---[NIEDIHFA]-ELRLYRRHHR----- | − | (SEQ ID NO:19) |
| pV8D2 | ---[NIEDIHFAND]-ELRLYRRHHR----- | − | (SEQ ID NO:20) |
| pV8Q | ---[NIEDIHFANDDQ]-ELRLYRRHHR----- | − | (SEQ ID NO:21) |

+,−: PRESENCE OR ABSENCE OF INCLUSION BODIES

☐ AMINO ACID SEQUENCE DERIVED FROM V8 PROTEASE (DESCRIBED FROM Asn (N) AT 209 POSITION FROM N-TERMINAL OF MATURE V8 PROTEASE)

Fig.14(a)

VILPNNDRHQITDTTNGHYAPVTYIQVEAPTGTFIASGVVVGKDTLLTNK 50
HVVDATHGDPHALKAFPSAINQDNYPNGGFTAENITKYSGEGDLAIVKFS 100
PNEQNKHIGEVVKPATMSNNAETQVNQNITVTGYPGDKPVATMWESKGKI 150
TYLKGEAMQYDLSTTGGNSGSPVFNEKNEVIGIHWGGVPNEFNGAVFINE 200
NVRNFLKQNIEDI 213 (SEQ ID NO:22)

Fig.14(b)

VILPNNDRHQITDTTNGHYAPVTYIQVEAPTGTFIASGVVVGKDTLLTNK 50
HVVDATHGDPHALKAFPSAINQDNYPNGGFTAENITKYSGEGDLAIVKFS 100
PNEQNKHIGEVVKPATMSNNAETQVNQNITVTGYPGDKPVATMWESKGKI 150
TYLKGEAMQYDLSTTGGNSGSPVFNEKNEVIGIHWGGVPNEFNGAVFINE 200
NVRNFLKQNIEDIH 214 (SEQ ID NO:23)

Fig.14(c)

VILPNNDRHQITDTTNGHYAPVTYIQVEAPTGTFIASGVVVGKDTLLTNK (50)
HVVDATHGDPHALKAFPSAINQDNYPNGGFTAENITKYSGEGDLAIVKFS (100)
PNEQNKHIGEVVKPATMSNNAETQVNCNITVTGYPGDKPVATMWESKGKI (150)
TYLKGEAMQYDLSTTGGNSGSPVFNEKNEVIGIHWGGVPNEFNGAVFINE (200)
NVRNFLKQNIEDIHF (215) (SEQ ID NO:24)

PROCESS FOR PRODUCTION OF PROTEIN

BACKGROUND OF INVENTION

1. Field of Invention

The present invention relates to a process for production of a desired polypeptide using gene recombination techniques. Preferably the desired polypeptides are physiologically active polypeptides, for examples enzymes such as proteases. For example, the present invention relates a process for production of derivatives of *Staphylococcus aureus* V8 protease.

As a more specific example, the present invention provides a process for production of an active V8 protease derivative by expressing an insoluble fusion protein of a V8 protease derivative of *Staphylococcus aureus* origin using an *E. coli* expressing system, excising the V8 protease derivative from the fusion protein with an ompT protease intrinsic in *E. coli* in the presence of a denaturating agent and if necessary refolding the V8 protease.

*Staphylococcus aureus* (*S. aureus*) V8 protease is one of the proteases secreted into a culture medium by *S. aureus* V8 strain. This enzyme was isolated and purified by Drapeau, G. R et al. in 1972, as one of the serine proteases, which is secreted into a culture medium of *S. aureus* V8 strain and specifically cleaves the C-terminal of glutamic acid and aspartic acid (Jean Houmard and Gabriel R. Drapeu (1972), Proc Natl. Acad. Sci. USA, 69, 3506–3509). A DNA nucleotide sequence of the enzyme was determined by Cynthia Carmona et al., in 1987 (Cynthia Carmona and Gregory L. Gray (1987), Nucleic Acids R s. 15, 6757).

It is believed that the present enzyme is expressed as a precursor having 336 amino acid residues, and secreted as a mature protein by deletion of a prepro sequence of 68 amino acid residues from the N-terminal of the precursor. In addition, it is known that the present enzyme has a repeat sequence of proline-aspartic acid-asparagine at the C-terminal region (amino acid numbers 221–256). It is not clear whether or not this repeat sequence is essential for enzymatic activity, and Gray et al. consider that the repeat sequence might function when the enzyme exists as an inactive enzyme prior to secretion.

Although the functions of this enzyme have not been fully analysed, since the enzyme specifically cleaves the C-terminal of glutamic acid and aspartic acid, it is extensively used for determination of an amino acid sequence of proteins. In addition, since the present enzyme acts on a substrate even in the presence of urea (at a concentration of about 2 M), it is used to liberate a desired peptide from its fusion protein, after solubilization, with urea, of a large amount of insoluble fusion protein intracellularly expressed according to a gene recombination technique.

The present inventors successfully used the above-mentioned method to efficiently produce human calcitonin by gene recombination techniques (Japanese Unexamined Patent Publication (Kokai) No. 5-328992, EP528686). In addition, the *S. aureus* V8 protease was used to excise human glucagon from a fusion protein expressed in the *E. coli* expression system (Kazumasa Yoshikawa et al. (1992), Journal of Protein Chemistry, 11, 517–525).

As can be seen from the above, the present enzyme has been extensively used for research and production of peptides by gene recombination. However, since the enzyme is purified from a culture medium of *S. aureus* V8, there are problems in that (1) the enzyme is contaminated with trace amounts of other proteins, (2) the *S. aureus* V8 is a pathogenic strain, and (3) the product is expensive.

SUMMARY OF THE INVENTION

Accordingly, an object of the present invention is to produce a large amount of a desired polypeptide such as *S. aureus* V8 protease. The production of a highly purified desired polypeptides such as *S. aureus* V8 protease is very advantageous in scientific research and industry and a method for industrial production of large amounts of polypeptides has been urgently sought.

Accordingly, the present invention provides a process for the production of a desired polypeptide comprising the steps of:

(1) transforming host cells with an expression vector comprising a gene coding for a fusion protein comprising a desired polypeptide and a protective polypeptide;

(2) culturing the transformed host cells so as to express said gene to produce the fusion protein; and (3) excising the desired polypeptide from the fusion protein with a protease intrinsic to the host cells.

According to a preferred embodiment of the present invention, there is provided a process for the production of a desired polypeptide, comprising the steps of:

(1) transforming *Escherichia coli* host cells with an expression vector comprising a gene coding for a fusion protein comprising at least one protective polypeptide, a desired polypeptide and a linker peptide, wherein the protective polypeptide is a polypeptide derived from *E. coli* β-galactosidase and/or a polypeptide derived from an amino glycoside 3'-phosphotransferase of transposone 903 origin, the desired polypeptide is a derivative of *Staphylococcus aureus* V8 protease, the linker peptide between said protective polypeptide and said desired polypeptide has a substrate site specifically recognized by a protease intrinsic to the host cells;

(2) expressing said gene in *E. coli* host cells to produce the derivative of the *Staphylococcus aureus* V8 protease as an inactive fusion protein;

(3) disrupting the cells so as to separate the fusion protein, and obtaining a fraction containing the *E. coli* ompT protease which is a protease intrinsic to the cells and the fusion protein;

(4) solubilizing the fusion protein with a denaturating agent; and (5) decreasing a concentration of the denaturating agent to a level at which the *E. coli* ompT protease exhibits its activity to cleave the linker peptide with the protease so as to obtain the desired polypeptide from the fusion protein.

BRIEF EXPLANATION OF DRAWINGS

FIG. 4(*a*) and FIG. 4(*b*) represent amino acid sequences encoded in plasmids pV8RPT(+) and pV8RPT(-).

FIG. 6 represents an amino acid sequence of a fusion protein encoded in the plasmid pV8D.

FIG. 7 represents a result of electrophoresis showing that the present fusion protein forms inclusion bodies and transfers to an insoluble fraction.

FIG. 9 represents a result of electrophoresis showing refolding of V8 protease liberated by the ompT protease.

FIG. 11 represents nucleotide sequences of primers used for construction of DNAs coding for various fusion proteins (pV8H, pV8F, pV8A, pV8D2 and pV8Q).

FIG. 13 represents C-terminal amino acid sequences of V8 protease encoded in plasmids pV8D, pV8H, pV8F, pV8A, pV8D2 and pV8Q, as well as formation of inclusion bodies from expression products (fusion proteins) of the plasmids.

FIG. 14(*a*), FIG. 14(*b*) and FIG. 14(*c*) represent an amino acid sequence of a desired polypeptide produced by a process of the present invention.

DETAILED DESCRIPTION

Figures 1A, 1B:
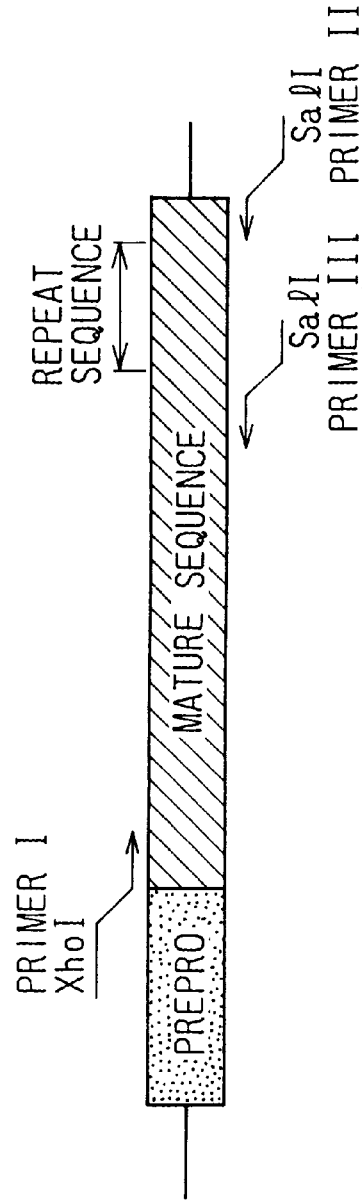
FIG. 1(*a*) and FIG. 1(*b*) represent (a) construction of a gene coding for *Staphylococcus aureus* (*S. aureus*) V8 protease, and (2) nucleotide sequence of PCR primes used to clone the gene of the present invention.

To carry out the present invention, a gene coding for a desired polypeptide, for example a gene coding for *S. aureus* V8 protease, is isolated from, for example, *S. aureus* V8 or is synthesized, the gene thus obtained is introduced into safe host cells such as *E. coli* cells, and the desired polypeptide, such as an enzyme, is produced with a low cost.

Generally to produce a desired polypeptide or protein by genetic engineering, preferably the desired polypeptide or protein is formed as a fusion protein and the polypeptide or protein is intracellularly accumulated as insoluble inclusion bodies, so as to prevent the bad effects of the produced polypeptide or protein on the growth and survival of the host cell as well as expression of the desired polypeptide or protein.

However, in some cases according to a conventional procedure a fusion protein comprising a desired polypeptide or protein does not forms inclusion bodies. In such cases, according to the present invention both of the C-terminal and N-terminal of a desired polypeptide or protein are linked with protective peptides through linker peptides to form an insoluble fusion protein so as to form inclusion bodies.

According to an embodiment of the present invention, a fusion protein comprising a desired polypeptide or protein is intracellularly accumulated as inclusion bodies. Although a protease intrinsic to host cells does not act on the inclusion bodies, said protease accompanying the inclusion bodies acts on the fusion protein after the inclusion bodies are isolated and the fusion protein is dissolved, so as to cleave the fusion protein resulting in liberation of the desired polypeptide or protein. In this way, according to the present invention, a desired polypeptide or protein with high purity can be efficiently produced using genetic engineering.

As an example of the production of a desired polypeptide or protein according to the present invention, a process for a large-scale production of *S. aureus* V8 protease with high purity using the *E. coli* expression system is described in detail.

First, the present inventors considered that to produce a large amount of *S. aureus* V8 protease using an *E. coli* expression system, it is preferable to express the protease as an enzymatically inactive fusion protein, because it is considered that if the present protease is directly expressed in host cells the protease hydrolyses *E. coli* proteins resulting in termination of the growth of the host cells, and a large amount of *S. aureus* V8 protease cannot be obtained.

Accordingly, the present inventors planned to express the desired protein as an enzymatically inactive fusion protein, to excise an enzymatically active *S. aureus* V8 protease moiety from the fusion protein with another protease, to refold the excised V8 protease and to purify the active *S. aureus* V8 protease.

In addition, the present inventors considered the use of ompT protease considered to exist in the outer membrane of *E. coli* cell as the protease for cleaving the fusion protein, because it is considered that the addition of another enzyme increases the production cost.

The use of ompT protease intrinsic in *E. coli* cells has advantages in that (1) the production process is simple; (2) the addition of an additional enzyme into the reaction system is not necessary resulting in a low production cost; and (3) since the use of V8 protease separately produced by other host is not necessary, incorporation of proteins contaminated in the V8 protease preparation (for commercially available V8 protease, *S. aureus*-derived proteins) into the product can be prevented.

*E. coli* ompT protease exists in an *E. coli* outer membrane fraction and selectively cleaves a bond between two basic amino acids (Keijiro Sugimura and Tatsuro Nishihara (1988), J. Bacteriol. 170, 5625–5632). Sugimura et al. purified the ompT protease, subjected various peptides to cleavage with the ompT protease at 25° C. for 30 minutes, and reported that the ompT protease cleaves a bond between two basic amino acids, i.e., a bond between arginine-arginine, lysine-arginine, lysine-lysine and lysine-arginine. However, they did not refer to whether or not the ompT protease is active in the presence of urea (urea concentration 2 M or more). It is considered that since the ompT protein occurs in the outer membrane, the ompT protease coprecipitates with a precipitation fraction after producing *S. aureus* V8 protease as inclusion bodies in *E. coli* cells, disrupting the *E. coli* cells and centrifuging the disruptant to separate an insoluble fraction.

To the precipitated fraction thus obtained is added urea to solubilize the fusion protein comprising *S. aureus* V8 protein. The present inventors considered that if ompT protease activity is maintained in the above condition, the ompT protease could be used to excise *S. aureus* V8 protease from the fusion protein, and a large amount of *S. aureus* V8 protease could be produced by a simple process by refolding the excised protease to regenerate the active enzyme.

Next, the present invention is explained in detail. It was reported on the basis of a nucleotide sequence of *S. aureus* V8 protease gene that there are a signal sequence (pre sequence) necessary for secretion and a pro sequence, whose function is not clear, at the N-terminal of mature protein, and the above-mentioned repeat sequence at the C-terminal of the mature protein. Accordingly, a gene I coding for a mature protein from its N-terminal to C-terminal, and a gene II lacking the repeat sequence whose function is not known were prepared. Although it is not clear whether the repeat sequence whose function is not known is essential for enzyme activity, the present inventors considered that if this repeat sequence is not necessary, by deleting this repeat sequence resulting in lowering the molecular weight the number of molecules of the expressed protein per cell can increase resulting in an amount of the expressed protein.

Accordingly, chromosomal DNA preparation was isolated from *Staphylococcus aureus* V8 (ATCC 27733), and two V8 protease derivative genes I and II were prepared by PCR. To express these derivatives, plasmids pV8RPT(+) and pV8RPT(−) were constructed wherein an *E. coli* β-galactosidase derivative was used as a protective peptide in a fusion protein. In these plasmids a gene coding for *E. coli* β-galactosidase derivative and a gene coding for V8 protease derivative (I or II) are linked with a gene coding for a linker peptide containing arginine-arginine which is recognized and cleaved with ompT protease, under the regulation by a lactose promoter, to express a fusion protein.

It was considered that for the fusion protein thus designed it is possible to express a V8 protease derivative as insoluble fusion protein, to solubilize the fusion protein using urea, to cleave the fusion protein with ompT protease by decreasing urea concentration so as to separate the *E. coli* β-galactosidase derivative protein and the V8 protease derivative protein.

The plasmids as designed above were constructed, and induced to express the fusion protein in *E. coli* host cells with isopropyl-β-D-thio-galactopyranoside (IPTG). As a result the two fusion proteins did not become insoluble, and after disruption of the cells, enzyme activity was detected in the supernatants.

On the other hand, after induction with IPTG, the growth of the cells remarkably decreased. It was observed from an analysis by SDS polyacrylamide gel electrophoresis that intracellular proteins were degraded by enzymatic activity of expressed V8 protease derivative. Therefore, it was clarified that in a method wherein a fusion protein comprising the *E. coli* β-galactosidase derivative and V8 protease derivative is expressed, (1) an expressed enzyme has an enzymatic activity and inhibits the growth of host cells; and (2) since an amount of an expressed protein is very low said method is not suitable for the production of V8 protease derivative.

However, it was considered from the above-mentioned results that, (1) the pro-sequence of the N-terminal probably does not involve refolding of V8 protease; and (2) the repeat sequence is possibly not necessary for V8 protease activity because V8 protease derivative II not having the C-terminal repeat sequence was active.

Next, to produce an active V8 protease by expressing V8 protease as an insoluble fusion protein in an *E. coli* expression system, solubilizing the fusion protein with urea, liberating V8 protease from the fusion protein using a protease in the presence of urea and by refolding the liberated V8 protease, the present inventors started experiments on the basis of the following assumption.

(1) When the above-mentioned *E. coli* β-galactosidase was fused to the N-terminal of V8 protease, the resulting fusion protein was not insoluble. Therefore, the present inventors planned to add additional protective peptide to the above-mentioned fusion protein to form an insoluble fusion protein, and tried to use an aminoglycoside 3'-phosphotransferase protein desired from a kanamycine resistance gene of transposone 903 (Nucleic Acids Res. (1988) 16,358). Namely, the present inventors considered adding a part of aminoglycoside 3-phosphotransferase protein to the C-terminal of a fusion protein comprising a *E. coli* β-galactosidase derivative and V8 protease, through a linker peptide to promote insolubilization of a fusion protein so as to form inclusion bodies.

In addition, (2) the present inventors expected that if the above-mentioned R6 linkers are positioned at the N- and C-terminals of the V8 protease, the V8 protease can be liberated from the fusion protein by cleaving the fusion protein with the ompT protease which cleaves a bond between two basic amino acids.

Accordingly on the basis of the above-mentioned assumption, a novel expression plasmid, pV8D which expresses a fusion protein comprising a part of aminoglycoside 3'-phosphotransferase fused to an *E. coli* β-galactosidase derivative/V8 protease derivative fusion protein was constructed. Note that the V8 protein derivative encoded by this plasmid (designated V8D protein hereinafter) lacks C-terminal 8 amino acids in comparison to the above-mentioned V8 protease derivative II, and the N-terminal and C-terminal of this V8D have been fused to an *E. coli* β-galactosidase derivative and part of aminoglycoside 3'-phosphotransferase through the R6 linker peptides.

*E. coli* JM101 having pV8D was cultured, and induced with IPTG, and it was found from SDS PAGE that a fusion protein of about 60 kd thus expressed intracellularly formed insoluble inclusion bodies.

Next, the cultured cells were disrupted, and the disruptant was centrifuged to isolate inclusion bodies comprising a fusion protein, which were then dissolved by a denaturing agent such as urea, guanidine hydrochloride or a surfactant.

In Examples of the present invention, the inclusion bodies were dissolved with 8 M urea, and the mixture was diluted to make the urea concentration 4 M, and the whole was incubated at 37° C. for 2 hours. It was confirmed that under this condition ompT protease intrinsic to *E. coli* cleaved the fusion protein and provided, in SDS PAGE analysis, 12 KDa, 26 KDa and 22 KDa bands corresponding to β-galactosidase derivative, V8D protein and a part of aminoglycoside 3'-phosphotransferase protein respectively.

On the other hand, when the same experiment was carried out using as host *E. coli* W3110M25 which is an ompT deficient mutant, the above-mentioned bands were not detected revealing that a protease which specifically cleaved the fusion protein was an ompT protease intrinsic to *E. coli*. In addition, to confirm that the fusion protein was specifically cleaved with ompT protease, a 26 KDa band corresponding to the V8D protein was extracted from the SDS-PAGE gel, and N-terminal amino acid sequence thereof was determined. As a result, it was confirmed that a bond between arginine-arginine in the R6 linker peptide was cleaved.

Accordingly, it was found for the first time by the present inventors that both the fusion protein and the ompT protease were present in the inclusion bodies precipitated by centrifugation, and after solubilization of the inclusion bodies with 8 M urea, the ompT protease was fully active in the presence of 4 M urea and precisely cleaved the expected site of the amino acid sequence.

It is considered that the enzyme activity of the product is very low because the V8 protease derivative protein formed in the presence of urea was denatured. Therefore, the present inventors carried out refolding of the V8D proteins, if necessary, by lowering the concentration of the denaturing agent so as to determine whether an entimatically active V8D protein can be obtained. After the cleave reaction with the ompT protease, a sample was diluted 20-fold with 0.4 M potassium phosphate buffer (pH 7.5), and allowed to stand overnight on ice. By this operation, about 20% of the V8D protein was refolded and recovered it enzymatic activity. After this operation, a sample was analysed by SDS-PAGE. As a result, after refolding, a major protein was the V8D protein.

The reason of this phenomenon is considered that although prior to refolding a β-galactosidase derivative, a part of aminoglycoside 3'-phosphotransferase protein and *E. coli*-derived proteins were present, after the refolding the V8D protease having protease activity hydrolized other accompanied proteins. This result is very advantageous for purification of the V8D protein after refolding.

Next, it was tested whether the V8D protease activated as described above has the same substrate specificity as that of native *S. aureus* V8 protease. A substrate (for example a fusion protein comprising a human calcitonine derivative) was reacted with a refolded V8D protease and a native enzyme at 30° C. for an hour, and peptide fragments generated from a fusion protein by cleavage with the enzyme ware analysed by a high performance liquid chromatography. As a result, elution patterns of the peptide fragments generated by both of the enzymes were same, revealing that the V8D protein prepared as descried above has the same substrate specificity as that of the native enzyme.

To intracellularly express the *S. aureus* V8 protease as insoluble inclusion bodies, said protease should not act on the fusion protein. On the other hand, after refolding, said protease should exhibit its enzymatic activity. Such apparently discrepant properties are requested to V8 protease derivative protein. For the V8D protease, a fusion protein comprising a part of native V8 protease starting from the N-terminal and ending at the 212nd amino acid was constructed, and the C-terminal of said V8 protease portion was extended and fused to a part of aminoglycoside 3'-phosphotransferase protein to form a fusion protein, and the fusion protein was tested whether it forms inclusion bodies and whether it is reactivated by refolding.

Namely, the present inventors constructed expression plasmids pV8H, pV8F, pV8A, pV8D2 and pV8Q expressing fusion proteins of the V8 protease which C-terminal is extended by 2, 4, 6 and 8 amino acid residues respectively by PCR method and gene cloning. These plasmids were used to transform *E. coli* JM101 to construct transformats. The resulting transformats were cultured and induced with IPTG. As a result, the transformats having the plasmids pV8D, pV8H or pV8F formed inclusion bodies of fusion protein and after cleavage of the fusion protein by ompT protease, refolded enzymes were reactivated. On the other hand, other transformats did not form inclusion bodies, and after disrupting the cultured cells, the soluble fraction exhibited V8 protease activity. Accordingly, it was found that the *E. coli* V8 protease derivative protein should fuse at its 215th phenylalanine or an amino acid before the 215th amino acid with a protective polypeptide to form inclusion bodies of the fusion protein, followed by enzymatical cleavage of the fusion protein and refolding.

Although the present invention was explained by taking V8 protease as an example of desired polypeptide, the same principle and procedure can apply to other desired polypeptides or protein such as motilin, glucagon, adrenocorticotrophic hormone (ACTH), corticotropin-releasing hormone (CRH), secretin, growth hormone, insulin, growth hormone-releasing hormone (GRH), vasopressin, oxytocin, gastrin, glucagon-like peptide (GLP-1, GLP-2, 7–36 amide), cholecystokinin, vasoactive intestinal polypeptide (VIP), pituitary adenolate cyclase activating polypeptide (p.a.c.a.p.), gastrin releasing hormone, galanin, thyroid-stimulating hormone (TSH), luteinizing hormone-releasing hormone (LH-RH), calcitonin, parathyroid hormone (PTH, PTH(1–34), PTH(1–84), peptide histidine isoleucine (PHI), neuropeptide Y (nP.Y)), peptide YY (P.YY), pancreatic polypeptide (P.P.), somatostatin, TGF-α, TGF-β, nerve growth factor, fibroblast growth factor, relaxin, prolactin, atrial natriuretic peptide (ANP), B-type natriuretic peptide (BNP), C-type natriuretic peptide (CNP), angiotensin, brain derived nutrient factor (BDNF) and further enzymes such as KEX2 endoprotease, to efficiently produce such desired polypeptides or proteins.

Accordingly, the present invention provides a process for production of a desired polypeptide characterized by transforming host cells with an expression vector containing a gene coding for a fusion protein comprising a protective polypeptide and a desired polypeptide, expressing the gene to produce the fusion protein and excising the desired polypeptide by a protease intrinsic to the host cells.

According to the present invention, the fusion protein can be represented by the formula (1) A-L-B or (2) A-L-B-L-C, wherein A and C represent protective polypeptides, B represents a desired polypeptide and L represents a linker peptide containing a substrate site recognized by a protease intrinsic to the host cells, and the fusion protein is cleaved in the linker peptide L so as to obtain the desired polypeptide from the fusion protein.

According to a preferred embodiment of the present invention, the desired polypeptide is a biologically or physiologically active polypeptide, preferably an enzyme, and more preferably proteolytic enzyme. In the most preferably embodiment of the present invention, the desired polypeptide is a protease, which is expressed in host cells as an inactive fusion protein, the host cells are disrupted to isolate the fusion protein which is then solubilized with a denaturating agent, and then the linker peptide region is cleaved with a protease intrinsic to the host cells to obtain the desired polypeptide from the fusion protein.

In another preferred embodiment, there is mentioned a process for production of a desired polypeptide wherein the desired polypeptide is a proteolytic enzyme, the desired polypeptide is expressed in host cells as an insoluble fusion protein comprising the desired polypeptide linked to a protective polypeptide through a linker peptide, the host cells are disrupted to isolate the fusion protein, the fusion protein is solubilized with a denaturating agent at a concentration at which a protease intrinsic to the host cells is not active, and the concentration of the denaturating agent is lowered to a level at which said intrinsic protease exhibits its enzymatic activity so that the intrinsic protease cleaves the linker peptide to obtain the desired polypeptide from the fusion protein. In this case, during the isolation process after the disruption of the cells, said intrinsic protease and the fusion protein preferably coexist in the same fraction.

The protective polypeptide may be any polypeptide which can be expressed as a part of a fusion protein comprising a desired polypeptide, and for example a polypeptide derived from *E. coli* β-galactosidase, a polypeptide derived from aminoglycaside 3'-phosphotransferase of transposon 903 origin etc. alone or in combination may be used.

Linker peptide is a peptide having a site specifically recognized by a protease intrinsic to the host cells which contain an expression vector for a desired polypeptide. A preferred embodiment of the linker peptide a polypeptide consisting of 2 to 50 amino acid resides and containing one or more pairs of two basic amino acid residues. A linker peptide may have the pairs of basic amino acid residues at both of the N- and C-terminal thereof.

The denaturating agent may be any substance which solubilizes a fusion protein and is for example urea, guanidine hydrochloride, surfactants etc. Urea is preferably used, and in this case a concentration of urea is preferably 1 to 8 M. Concentration of urea after solubilization of the fusion protein may be any concentration at which a protease intrinsic to host cells exhibit its enzymatic activity.

In the present invention relating to a process for production of a desired polypeptide wherein the desired polypeptide is expressed as a fusion protein and the fusion protein is cleaved with a protease intrinsic to host cells, the intrinsic protease and the desired polypeptide are not limited anyway. Namely, the intrinsic protease may be any protease capable of processing a fusion protein after the fusion protein is expressed as an insoluble protein, and is for example E. coli ompT protease used in Example or the like. The desired polypeptide may be any polypeptide consisting of preferably 20 to 800 amino acid residues, and for example S. aureus protease and/or a derivative thereof as shown in the Examples hereinafter.

According to the present process for production of a desired polypeptide using gene recombination technique, especially a V8 protease derivative protein may be produced in an E. coli expression system. Namely, a preferred embodiment for production of a desired polypeptide comprises the steps of:

(1) transforming Escherichia coli host cells with an expression vector comprising a gene coding for a fusion protein comprising at least one protective polypeptide, a desired polypeptide and a linker peptide, wherein the protective polypeptide is a polypeptide derived from E. coli β-galactosidase and/or a polypeptide derived from an aminoglycoside 3'-phosphotransferase of transposone 903 origin, the desired polypeptide is a derivative of Staphylococcus aureus V8 protease, the linker peptide between said protective polypeptide and said desired polypeptide has a substrate site specifically recognized by a protease intrinsic to the host cells;

(2) expressing said gene in E. coli host cells to produce the derivative of the Staphylococcus aureus V8 protease as an inactive fusion protein;

(3) disrupting the cells so as to separate the fusion protein, and obtaining a fraction containing the E. coli ompT protease which is a protease intrinsic to the cells and the fusion protein;

(4) solubilizing the fusion protein with a denaturating agent; and (5) decreasing a concentration of the denaturating agent to a level at which the E. coli ompT protease exhibits its activity to cleave the linker peptide with the protease so as to obtain the desired polypeptide from the fusion protein.

After refolding V8 protease derivative, this protein can be highly purified by conventional procedures for purification of protein, for example, gel filtration, ionic chromatography, hydrophobic chromatography. In addition, for the V8 protease derivative as shown in Examples, since after finishing the refolding reaction said derivative is the main proteinaceous component in the reaction mixture, the purification is very easy.

EXAMPLE

Next, the present invention is explained, in more detail, in following Examples.

Example 1

Isolation of S. aureus V8 protease gene

A V8 protease gene was prepared by PCR method on the basis of a reported nucleotide sequence. Three PCR primers shown in FIG. 1(b) were synthesized by a DNA sequencer (Applied Bio system). The primers I, II and III correspond to the regions of V8 protease gene and the primer I has at its 5'-terminal side a XhoI restriction enzyme site and the primers II and III have at their 5'-terminal side a SalI restriction enzyme site, as shown in FIG. 1. PCR was carried out using a chromosome prepared from Staphylococcus aureus V8 (ATCC 27733) by Jayaswal et al. method (J. Bacterial. 172: 5783–5788 (1990)) and the above-mentioned PCR primers. 2.5 units of Taq DNA polymerase was added to 50 $\mu$l of a reaction mixture containing 1.0 $\mu$M primers, 1 $\mu$g chromosomal DNA, 50 mM KCl, 10 mM Tris-HCl, pH 8.3, 1.5 mM $MgCl_2$, 0.01% gelatin, 200 $\mu$M dNTP (mixture of dATP, dCTP, dCTP and dTTP), and PCR of 90° C. for 1 minute, 72° C. for 2 minutes and 55° C. for 2 minutes was carried out for 30 cycles.

As a result, a gene for a mature V8 protease containing a repeat sequence but not containing a prepro sequence (protease gene derivative I, 0.8 kb) was obtained by the primers I and II, and a gene for V8 protease containing neither prepro sequence nor repeat sequence (V8 protease gene derivative II, 0.7 kb) was obtained by the primers I and III. Next, these genes were subjected to electrophoresis, purified with SUPREP-2 (Takara Shuzo), and cleaved with restriction enzymes XhoI and SalI to obtain V8 protease derivative gene fragments I and II having cohesive ends XhoI and SalI.

Example 2

Figure 2:
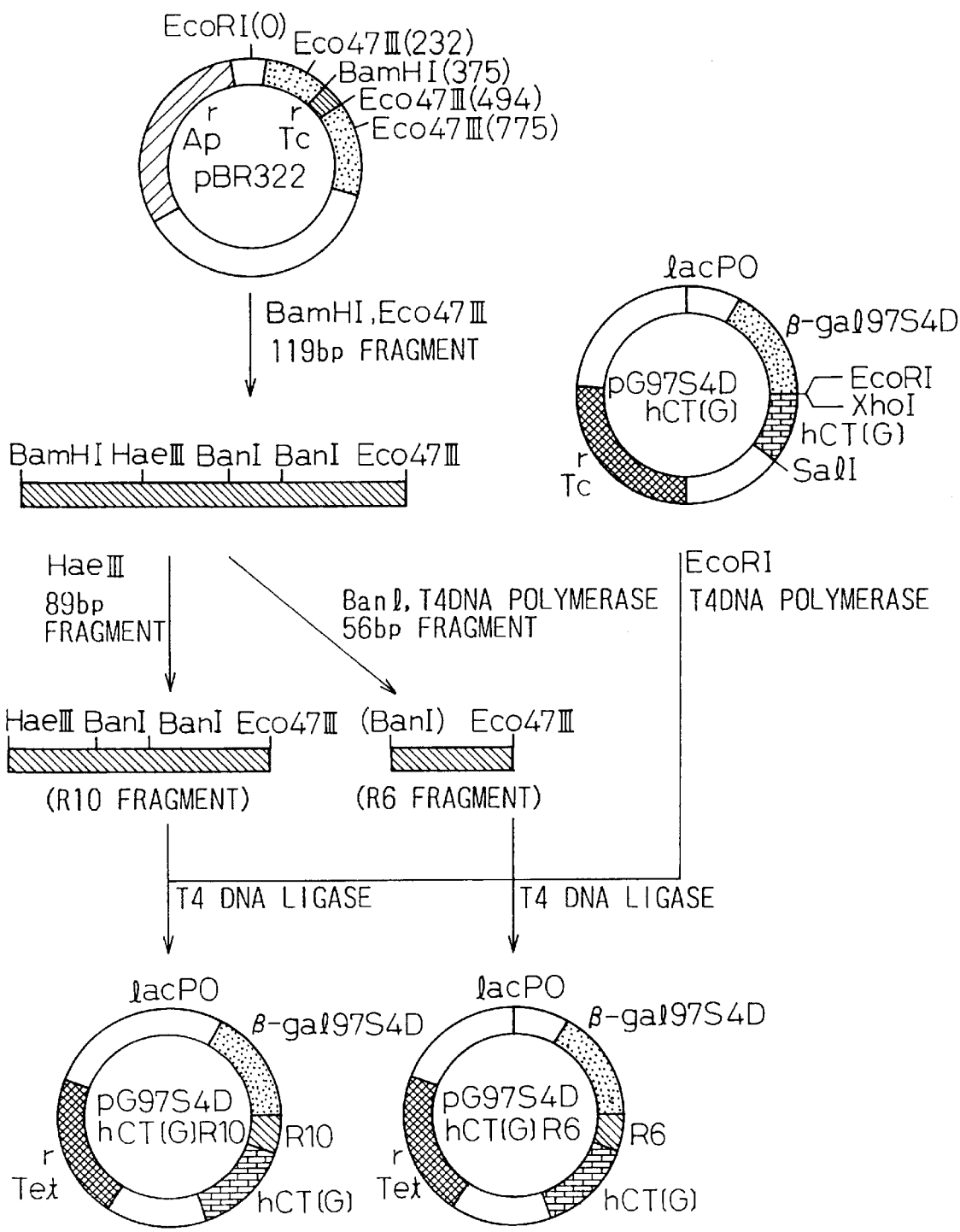
FIG. 2 represents processes for construction of pG97S4DhCT[G]R6 and pG97S4DhCT[G]R10.

Construction of expression vectors pV8RPT(+) and pV8RPT(-) as well as expression of V8 protease derivative A plasmid used in this Example, pG97S4DhCT[G]R6 is a plasmid which efficiently expresses a fusion protein comprising an E. coli β-galactosidase derivative and a human calcitonin precursor (hCT[G]), and can be constructed from plasmid pBR322 and plasmid pG97S4DhCT[G] (see, Japanese Unexamined Patent Publication No. 5-328992, EP528686, and FIG. 2). Escherichia coli W3110 containing the plasmid pG97S4DhCT[G] was designated Escherichia coli SBM323 and deposited with the National Institute of Bioscience and Human-Technology Agency of Industrial Science and Technology, 1–3 Higashi, 1-chome, Tsukuba-shi, Ibaraki-ken, Japan, on Aug. 8, 1991 as an international deposition under the Budapest Trealy as FERM BP-3503.

Figure 3:
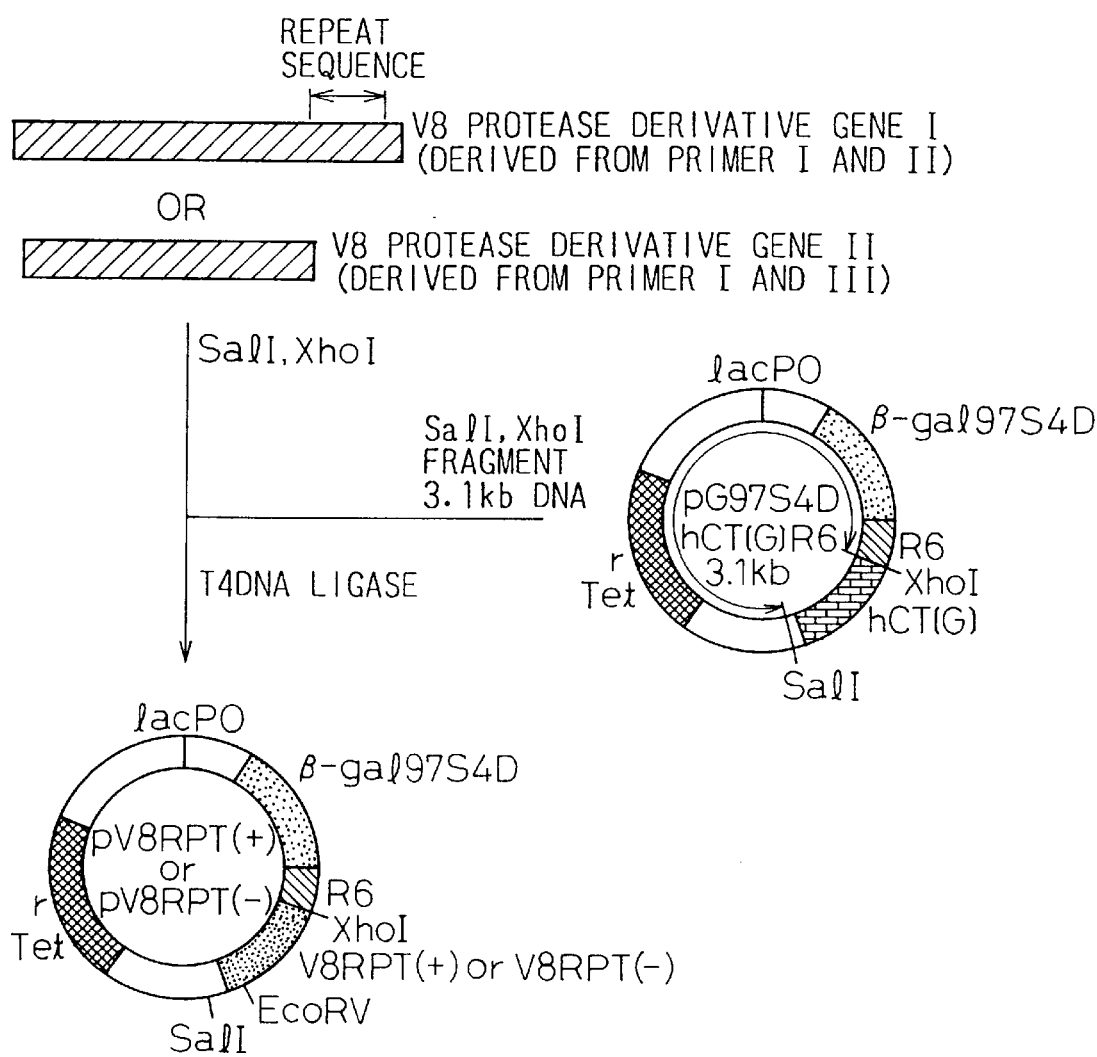
FIG. 3 represents processes of construction of plasmid pV8RPT(+) and pV8RPT(-).

To express the V8 protease genes I and II obtained by PCR, the plasmid pG97S4DhCT[G]R6 was digested with XhoI and SalI, and a DNA fragment (3.1 kb) lacking a human calcitonin precursor gene was prepared by agarose gel electrophoresis. This DNA fragment was joined to the V8 protease gene fragment having XhoI and SalI cohesive ends as prepared above using T4 DNA ligase, and the ligation product was used to transform E. coli JM101 so as to construct a plasmid pV8RPT(+) containing the V8 protease gene derivative I, and a plasmid pV8RPT(-) containing the V8 protease gene derivative II (FIG. 3). As a host for the plasmid, E. coli JM101 (available, for example, from Takara Shuzo, Invitrogen Catalog No. c660-00 etc.) was used. Amino acid sequences of fusion proteins comprising a V8 protease derivative and a β-galactosidase derivative, expressed by the above-mentioned plasmids are shown in FIG. 4. E. coli JM101/pV8RPT(+) and E. coli JM101/pV8RPT(-) were separately cultured in 100 ml of LB medium (0.5% yeast extract, 1.0% Trypton, 0.5% NaCl) at 37° C. until the absorbance OD660 reached 1.0, and the gene expression was induced by adding isopropylthiogalactopyranaside (IPTG) to the final concentration 2 mM. After the addition, culturing was further continued for 2 hours, and the culture was centrifuged to recover the microbial cells, which were then suspended in TE buffer (10 mM Tris-HCl (pH 8.0), 1 mM EDTA) at a concentration of OD660=5.

The cell suspension was treated with an ultrasonicator (cellruptor, Tosho Denski K.K.), the disruptant was centrifuged at 12,000 rpm for 5 minutes to eliminate an insoluble fraction, and the supernatant thus obtained was used as a crude enzyme preparation. The activity of V8 protease was measured using a synthetic substrate (Z-Phe-Leu-Glu-4-nitranilide; Boehringer Mamnnheim), 940 µl of 100 mM Tris-HCl (pH 8.0) buffer and 20 µl of 10 mM Z-Phe-Leu-Glu-4-nitranilide solution in DMSO were mixed, and to the mixture was added 40 µl of a crude enzyme solution. The mixture was incubated at room temperature for 5 minutes, and the absorbance, at 405 nm, of the reaction mixture was measured by a Hitachi spectrophotometer U-3200.

As a result, the crude enzyme solutions prepared from the cells of E. coli JM101/pV8RPT(+) and E. coli JM101/pV8RPT(−) provided an enzyme activity of 8 µg/ml, revealing that the enzyme in the form of a fusion protein with β-galactosidase and lacking a prepro sequence exhibits an enzyme activity. In addition, the product lacking C-terminal repeat sequence, encoded by pV8RPT(−) exhibited an enzyme activity, revealing that the repeat sequence is not essential for the enzyme activity.

Since the productivity of the V8 protease derivatives I and II by E. coli JM101/pV8RPT(−) and E. coli JM101/pV8RPT(+) was low and the bands thereof could not be detected by SDS-polyacrylamide gel electrophoresis (SDS-PAGE), then purification thereof was difficult. Considering the facts that the growth of the cells was ceased by the addition of IPTG and that the content of high molecular weight protein in induced cells was lower than that in non-induced cells, it was considered that a cause of low productivity is the fatal toxicity of V8 protease intracellularly expressed.

Example 3

Construction of expression vector pV8D

As can be seen from the above, since V8 protease fused at its N-terminal with β-galactosidase derivative has still its enzyme activity, the V8 protease cannot be inactivated by fusion only at its N-terminal. Accordingly the present inventors attempted to inactivate the V8 protease by further fusing the C-terminal thereof with a part of aminoglycosede 3'-phosphotransferase. To fuse the C-terminal of the V8 protease, the EcoRV site positioned before the repeat sequence was used.

Figure 5:
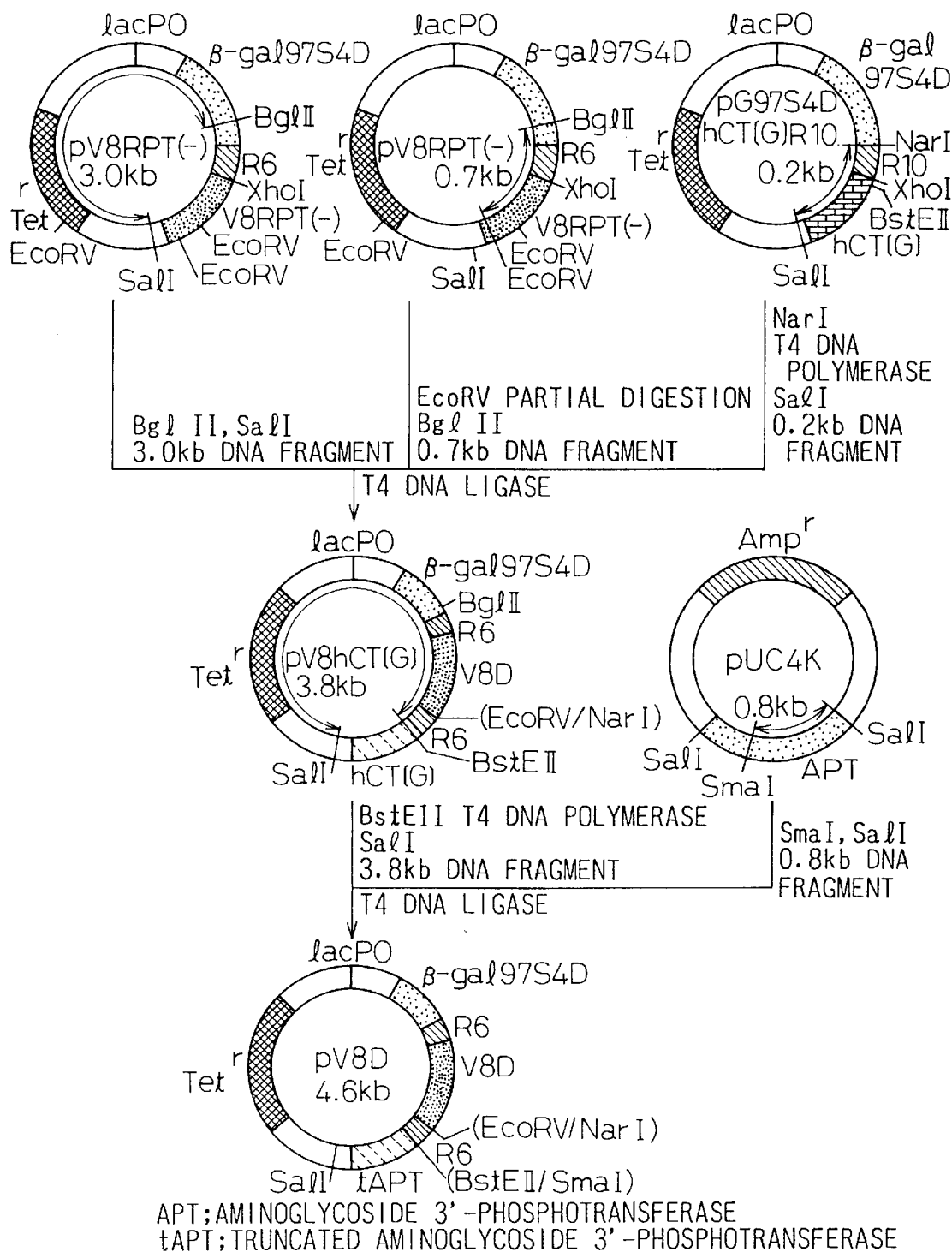
FIG. 5 represents a process for construction of plasmid pV8D.

The plasmid pV8D coding for a V8 protease derivative was constructed according to the procedure as shown in FIG. 5. Namely, a BglII-SalI fragment (3.0 kb) and an EcoRV-BglII fragment (0.7 kb) were prepared from pV8RPT(−1), a NarI-SalI fragment (0.2 kb) was prepared from pG97S4DhCT[G]R10, and these three DNA fragments were joined to obtain pV8hCT[G]. Note that the pG97S4Dh[G]R10 can be constructed from plasmid pBR322 and plasmid pG97S4DhCT[G] according to the same procedure for the above-mentioned plasmid pG97S4DhCT[G]R6 (see Japanese Unexamined Patent publication No. 5-328992, EP528686, FIG. 2).

Next, a hCT[G] region (0.1 kb BstEII-SalI fragment) in the pV8hCT[G] obtained as described above was replaced with a 0.8 kb SmaI-SalI fragment containing an aminoglycoside 3'-phosphotransferase gene region derived from pUC4K (Vieira, J. and Messing, J., Gene 19,259 (1982), Pharmacia Ca. No. 27-4958-01) to construct pV8D. An amino acid sequence of a fusion protein (V8D fusion protein) comprising V8 protease derivative expressed by said plasmid pV8D is shown in FIG. 6.

This fusion protein comprises V8 protease linked at its N-terminal and C-terminal with a β-galactosidase derivative and a part of aminoglycoside 3'-phosphotransferase respectively, through R6 linkers. The R6 linker has the sequence RLYRRHHRWGRSGSPLRAHE (SEQ ID NO: 1) wherein the peptide bond between R-R will be cleaved with ompT protease of E. coli.

Example 4

According to a conventional procedure, E. coli JM101/pV8D transformed with pV8D was cultured in 100 ml of LB medium at 37° C. until an absorbance OD660 reaches 0.6, and the production of fusion protein V8D was induced by adding IPTG to a final concentration 100 mM. After the addition, further culturing was continued for two hours, and the culture was centrifuged to recover the cultured cells. Contrary to the case of E. coli JM101/pV8RPT(+) and E. coli JM101/pV8RPT(−), in the case of the present strain, the growth of the cells was not terminated by the induction of expression of a fusion protein, and V8 protease activity was not detected in the cells.

In addition, the intracellular formation of inclusion bodies was microscopically observed. A result of 16% SDS-PAGE for cells as well as an insoluble fraction and a soluble fraction obtained by sonicating the cells, before and after the induction, is shown in FIG. 7. A large amount of V8D fusion protein of 60 kDa was contained in the induced cells, and in an insoluble fraction because inclusion bodies were formed. It is believed that the expression reached a level at which inclusion bodies were formed, because the V8 protease derivative fused at its C-terminal with a part of aminoglucoside 3'-phosphotransferase cannot take a native configuration and is inactive, and therefore it does not inhibit the growth of the cells. Note that in addition to the 60 kDa V8D fusion protein, a 27 kDa protein was detected in the insoluble fraction, and it was found that the 27 kDa protein is a fragment of the V8D fusion protein, which fragment comprised an amino acid sequence containing the 282nd methionine and following region.

Example 5

Processing of V8D fusion protein by ompT protease

Microbial cells obtained by culturing as shown in Example 4 were suspended in 10 ml of TE buffer, and disrupted by ultrasonic treatment. After that the inclusion bodies were recovered by centrifugation. The resulting inclusion bodies were re-suspended in 10 ml of deionized water, and the suspension was centrifuged to wash the inclusion bodies. The inclusion bodies were diluted with deionized water until the OD660 value reached 100, and 150 µl of the reaction mixture was taken. To the 150 µl sample were added 25 µl of 1 M Tris-HCl (pH 8.0), 2.5 µl of 1 M dithiothreitol (DTT) and 120 mg of urea to solubilize the inclusion bodies, and to the resulting solution was added deionized water to make total volume 500 µl. The resulting solution was heated at 37° C. for 2 hours.

Figures 8A, 8B:
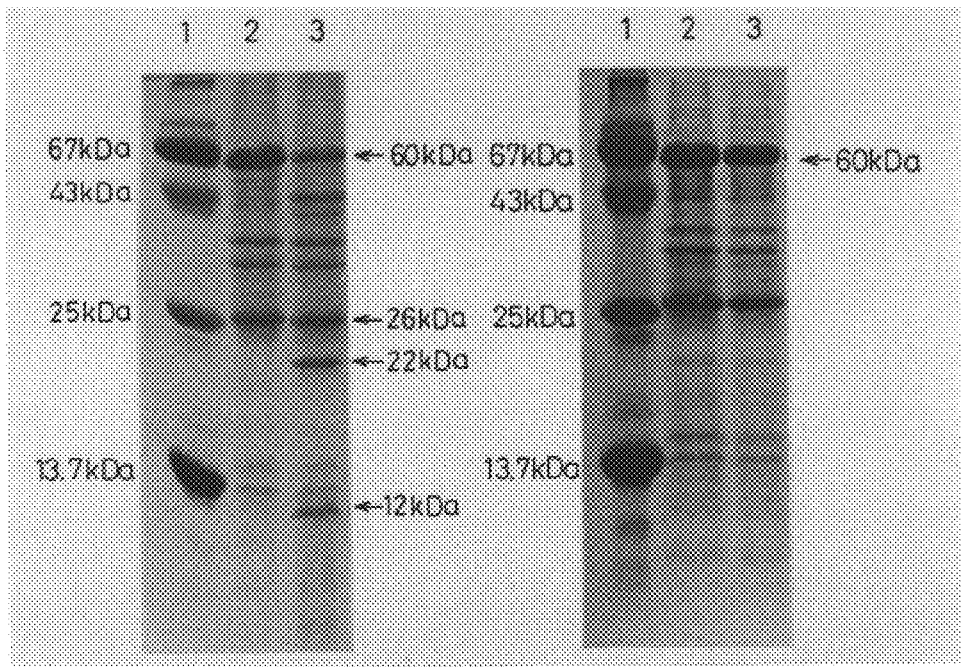
FIG. 8A and FIG. 8B represent a result of electrophoresis showing that the fusion protein V8D is cleaved by a host-derived protease ompT to liberate V8 protease.

FIG. 8A shows a result of 16% SDS-PAGE before and after the heating. As can be seen from FIG. 8A, a sample after the heating provided bands corresponding to β-galactosidase derivative, V8 protease derivative and a part of aminoglucoside 3'-phosphotransferase having molecular weights of 12 kDa, 26 kDa and 22 kDa respectively. On the other hand, FIG. 8B shows a result obtained by using a protease deficient strain *E. coli* W3110M25 (Sugimura, K. (1987) Biochem. Biophys. Res. Commun. 153, 753–759), expressing the V8D fusion protein and treating the inclusion bodies thus obtained according to the same procedure as described above. In this case, the above-mentioned three bands were not detected in SDS-PAGE, and therefore it was determined that the processing of the present fusion protein was a specific cleavage by ompT protease (Sugimura, K. and Nishihara, T. (1988) J. Bacteriol., 170, 5625–5632).

In addition, excision of the 26 kDa band from the SDS-PAGE and determination of N-terminal amino acid sequence of the fragment revealed that the band between R-R in the R6 sequence (RLYRRHHRWGRSGSPLRAHE) (SEQ ID NO: 1) was cleaved, and it was confirmed that the cleavage of the fusion protein was specifically carried out by ompT protease. During the above-mentioned operation, the solubilization of the inclusion bodies was carried out in the presence of 8 M urea, and the processing was carried out in the presence of 4 M urea, and therefore it was shown for the first time that the ompT protease is resistant to such a high concentration of urea, and can specifically cleave the fusion protein solubilized from the inclusion bodies.

Example 6

Refolding of recombinant V8 protease (V8D)

A sample after processing was diluted 20-fold with 0.4 M potassium phosphate buffer (pH 7.5), and allowed to stand overnight on ice. By this operation the recombinant V8 Protease (V8D) refolded, and exhibited an activity corresponding to 30 μg/ml as determined as described above. Ratio of refolding was about 20%. FIG. 9 shows a result of 16% SDS-PAGE before and after the refolding.

On refolding, the recombinant V8 protease (V8D) behaves as a strong protease on the β-galactosidase derivative, a protein derived from aminoglucoside 3'-phosphotransferase and other *E. coli*-derived proteins, which are therefore degraded and disappear. Accordingly, a sample after refolding contains the recombinant V8 protease (V8D) as a major protein, and therefore purification operation following the refolding may be extensively simplified.

The recombinant V8 protease (V8D) thus obtained lacks 56 amino acid residues at the C-terminal due to the construction of the gene, in comparison with the native V8 protease, but maintains its activity, revealing that this lacking region is not essential for the enzyme activity.

Example 7

Substrate specificity of recombinant V8 protease obtained by refolding from inclusion bodies To compare substrate specificity of recombinant V8 protease obtained by refolding with that of native V8 protease, an experiment was carried out wherein both of the proteases act on a fusion protein of a calcitonin precursor (hCT[G]) as a substrate to liberate hCT[G]. The calcitonin fusion protein used in the experiment comprises a β-galactosidase derivative (108 amino acid residues) and hCT[G] linked through a linker having glutamic acid, and native V8 protease cleaves the peptide bond of the carboxy side of the glutamic acid to liberate hCT[G]. Note that as a plasmid coding for said fusion protein, pG97S4DhCT[G]R4 can be mentioned (see Japanese Unexamined Patent Publication No. 5-328992, EP528686).

An amount of recombinant V8 protease (V8D) corresponding to an activity of 1.2 μg of native V8 protease was added to 1 ml of a solution containing 10 mM Tris-HCl (pH 8.0), 1 mM EDTA, 5 mM DTT, 2 M urea and 10 mg/ml human calcitonin fusion protein, the mixture was reacted at 30° C. for one hour, and the reaction mixture was analyzed by high performance liquid chromatography wherein elution was carried out using 0.1% trifluoroacetic acid (TFA) and 0.1% TFA/50% acetonitrile. Note that the recombinant V8 protease (V8D) was used after refolding without further purification, and a commercially available native V8 protease was used as a control.

Figure 10A:
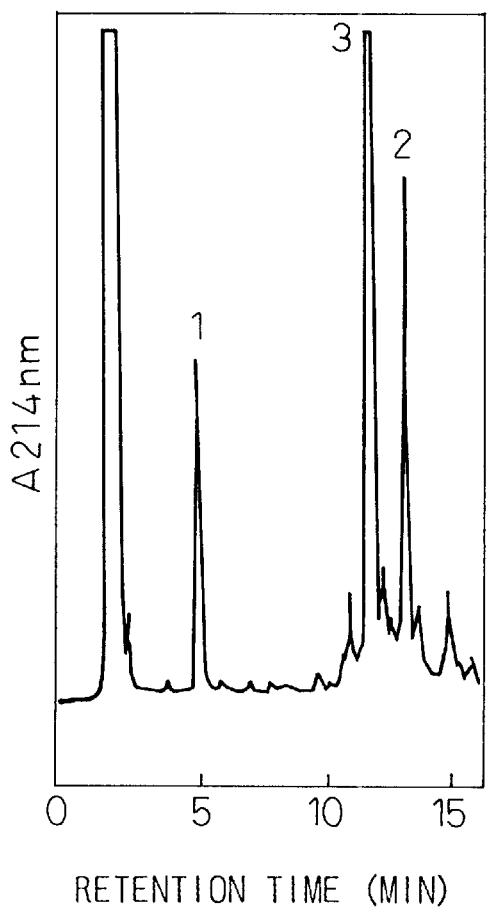
FIG. 10A and FIG. 10B are a chart comparing products formed from a fusion protein comprising a human calcitonin precursor by cleaving the fusion protein by (A) a recombinant V8 protease obtained by the present method and by (B) V8 protease obtained from *S. aureus*.
Figure 10B:
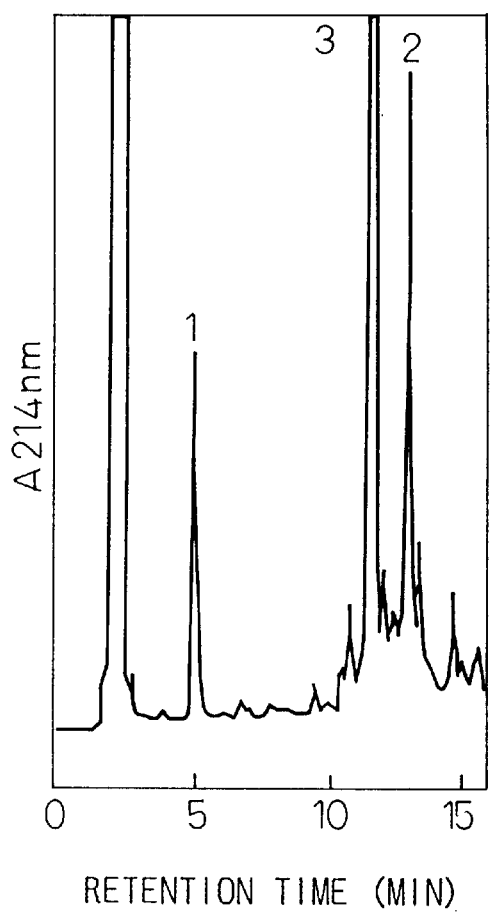

FIG. 10 shows an elution pattern of the high performance liquid chromatography.

Cleavage patterns of the recombinant V8 protease and the native V8 protease on the human calcitonin fusion protein were same, confirming that substrate specificity of both of the proteases is same.

Example 8

Study of fusion site at C-terminal side of V8 protease

To construct fusion proteins of V8 protease whose C-terminal is extended by 2, 3, 4, 6 and 8 amino acid residues respectively, in comparison with the V8D fusion protein, PCR primers shown in FIG. 11 were synthesized. A plasmid pV8F coding for a fusion protein extended by 3 amino acid residues (V8F fusion protein) was constructed as follows.

Figure 12:
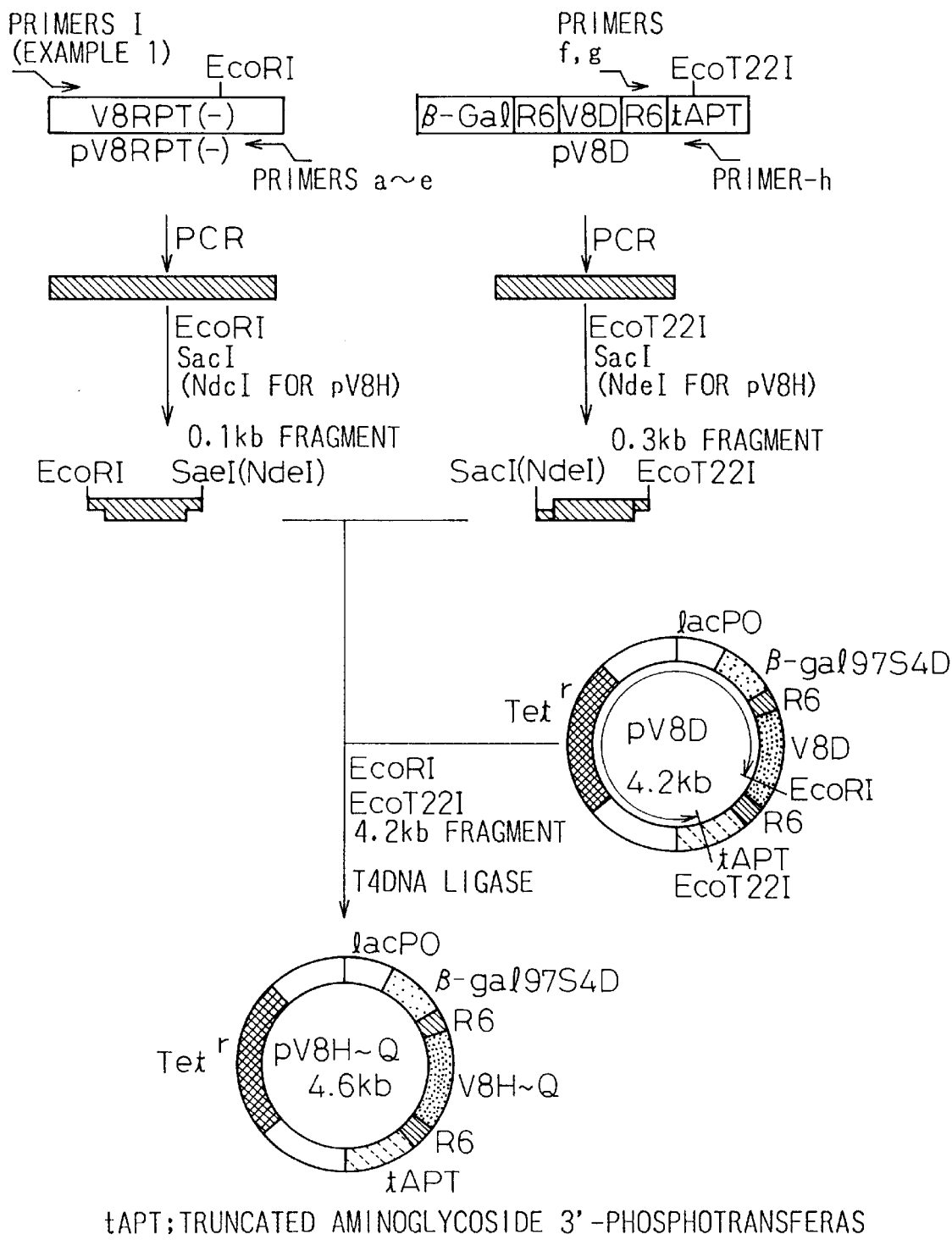
FIG. 12 represents a process for construction of plasmids pV8H, pV8F, pV8A, pV8D2 and pV8Q.

Namely, V8 protease gene was amplified using the primer b and the primer I shown in FIG. 1(*b*), and using as a template 0.1 μg of pV8RPT(-) constructed in Example 1, the amplified DNA fragment was cleaved with EcoRI and SacI to prepare a 0.1 kb gene fragment. On the other hand, a R6 linker sequence and aminoglucoside 3'-phosphotransferase gene region was amplified using the primer g and primer h, and 0.1 μg of pV8D as a template DNA, and the amplified DNA fragment was cleaved with EcoT22I and SacI to prepare a 0.3 kb gene fragment. Note that the PCR was carried out under the same condition as described in Example 1. The 0.1 kb and 0.3 kb gene fragments obtained as described above and the EcoRI-EcoT22I fragment (4.2 Kb) of pV8D were joined to construct pV8F (see, FIGS. 12 and 14).

Plasmid pV8H, pV8A, pV8D2 and pV8Q were constructed using primer g and primers a, c, d and e respectively according to the same procedure as described above (except that NdeI was used in place of SacI for construction of pV8H). Combinations of primers and template DNAs used for construction of the above plasmids are as follow.

pV8H: primer a, primer I and pV8RPT(-) as well as PCR product obtained by a combination of primer f, primer h and pV8D;

pV8A: primer c, primer I and pV8RPT(-) as well as PCR product obtained by a combination of primer g, primer h and pV8D;

pV8D2: primer d, primer I and pV8RPT(-) as well as PCR product obtained by a combination of primer g, primer h and pV8D; and pV8Q: primer e, primer I and pV8RPT(-) as well as PCR product obtained by combination of primer g, primer h and pV8D.

These plasmids produce fusion proteins comprising V8 protease region whose C-terminal is extended by 2, 4, 6 and 8 amino acid residues respectively in comparison with the V8D fusion protein shown in Example 4 (see, FIGS. 13 and 14).

These plasmids were used to transform *E. coli* JM101, and expression of each fusion protein was tested according to the same procedure as described in Example 4. The result is shown in FIG. 13. Inclusion bodies were formed from pV8H, pV8F and pV8D, and the inclusion bodies thus obtained were converted to refolded active V8 proteases according to the same procedure as described in Example 5. On the other hand, pV8A, pV8D2 and pV8Q did not form inclusion bodies, and V8 protease activity was detected in a soluble fraction. In the case of these plasmids, it is considered that the inclusion bodies are not formed because the expressed fusion proteins have protease activity and inhibit the growth of host cells. Namely, it was found that to express V8 protease as an inactive fusion protein, it is important to fuse V8 protease at its 215th phenylalanine or an amino acid before (nearer to the N-terminal) said phenylalanine with a protective polypeptide, and if the V8 protease fuses at an amino acid after (nearer to the C-terminal) the 215th phenylalanine, since a fusion protein whose V8 protease moiety forms a native configuration exhibiting protease activity is produced, the growth is repressed resulting in low expression.

According to the present invention, a large amount of a desired polypeptide can be produced with a low cost. Especially, according to the present invention, a large amount of *S. aureus* V8 protease can be efficiently produced with low cost using safe host such as *E. coli* according to gene recombination procedures.

We claim:

1. A process for production of a desired polypeptide comprising the steps of:
   (1) transforming host cells with an expression vector comprising a gene coding for a fusion protein comprising a desired polypeptide and a protective polypeptide;
   (2) culturing the transformed host cells so as to express said gene to produce an insoluble fusion protein, which forms inclusion bodies, wherein said inclusion bodies further comprise a protease intrinsic to said host cells; and
   (3) excising the desired polypeptide from the fusion protein with said protease.

2. A process according to claim 1, wherein the fusion protein is represented by the formula (1) A-L-B, or (2) A-L-B-L-C, wherein A and C are protective polypeptides, B is a desired polypeptide and L is a linker peptide containing a substrate site specifically recognized by a protease intrinsic to the host cells, and the fusion protein is cleaved in the linker peptide L region so as to obtain the desired polypeptide B.

3. A process according to claim 2, wherein the desired polypeptide is a physiologically active polypeptide.

4. A process according to claim 3 wherein the physiologically active polypeptide is selected from the group consisting of motilin, glucagon, adrenocorticotrophic hormone (ACTH), corticotropin-releasing hormone (CRH), secretin, growth hormone, insulin, growth hormone-releasing hormone (GRH), vasopressin, oxytocin, gastrin, glucagon-like peptide (GLP-1, GLP-2, 7–36 amide), cholecystokinin, vasoactive intestinal polypeptide (VIP), pituitary adenolate cyclase activating polypeptide (p.a.c.a.p.), gastrin releasing hormone, galanin, thyroid-stimulating hormone (TSH), luteinizing hormone-releasing hormone (LH-RH), calcitonin, parathyroid hormone (PTH, PTH(1–34), PTH (1–84), peptide histidine isoleucine (PHI), neuropeptide Y (nP.Y)), peptide YY (P.YY), pancreatic polypeptide (P.P.), somatostatin, TGF-α, TGF-β, nerve growth factor, fibroblast growth factor, relaxin, prolactin, natriuretic peptide, angiotensin, and brain derived nutrient factor.

5. A process according to claim 4, wherein the natriuretic peptide selected from the group consisting of ANP, BNP and CNP.

6. A process according to claim 3, wherein the physiologically active polypeptide is an enzyme.

7. A process according to claim 6, wherein the enzyme is KEX2 endopeptidase.

8. A process according to claim 6, wherein the enzyme is a proteolytic enzyme.

9. A process according to claim 8, further comprising the steps of:
   (a) expressing the desired polypeptide as an inactive fusion protein in host cells;
   (b) disrupting said host cells;
   (c) separating the fusion protein;
   (d) solubilizing the fusion protein with a denaturating agent; and
   (e) cleaving the linker peptide region with a protease intrinsic to the host cells so as to obtain the desired polypeptide from the fusion protein.

10. A process according to claim 9, wherein the protease intrinsic to the host cells and the fusion protein exist in the same fractions during an isolation process after the cell disruption.

11. A process according to claim 9, wherein the step (e) is carried out by decreasing a concentration of the denaturating agent.

12. A process according to claim 1, wherein the protease intrinsic to the host cells is *E. coli* ompT protease.

13. A process according to claim 9, wherein the denaturating agent for solubilization of the fusion protein is selected from the group consisting of urea, guanidine hydrochloride and surfactants.

14. A process according to claim 13, wherein the denaturating agent is 1 to 6 M urea.

15. A process according to claim 9, wherein the protease intrinsic to the host cells is *E. coli* ompT protease, and the fusion protein is cleaved with said protease in a solution containing 1 to 6 M urea.

16. A process according to claim 2, wherein the linker peptide has a site specifically recognized by a protease intrinsic to the host cells comprising an expression vector for the desired polypeptide.

17. A process according to claim 2, wherein the linker peptide consists of 2 to 50 amino acid residues and contains 1 or 2 pairs of basic amino acids.

18. A process according to claim 17, wherein the linker peptide has the basic amino acid pairs at the N-terminal and the C-terminal of the linker peptide.

19. A process according to claim 17, wherein the linker peptide has the amino acid sequence RLYRRHHRWGRSGSPLRAHE (SEQ ID NO: 1).

20. A process according to claim 1, wherein the desired polypeptide has 20 to 800 amino acid residues.

21. A process according to claim 8, wherein the proteolytic enzyme is *Staphylococcus aureus* V8 protease or a derivative thereof having the amino acid sequence of SEQ ID No. 7 from amino acid 125 to amino acid 336 and having protease activity.

22. A process according to claim 8, wherein the proteolytic enzyme is *Staphylococcus aureus* V8 protease or a derivative thereof having protease activity and having the amino acid sequence selected from the group consisted of SEQ ID NO:5 from amino acid 125 to amino acid 344, SEQ ID NO:6 from amino acid 125 to amino acid 392, SEQ ID NO:22, SEQ ID NO:23, or SEQ ID NO:24.

23. A process according to claim 1, wherein the protective polypeptide is a polypeptide derived from *E. coli* β-galactosidase and/or polypeptide derived from aminoglycoside 3'-phosphotransferase of transposone 903 origin.

24. A process according to claim 2, wherein the protective polypeptide A is a polypeptide derived from *E. coli* β-galactosidase, and the protective polypeptide C is a polypeptide derived from aminoglicoside 3'-phosphotransferase of transposone 903 origin.

25. A process according to claim 12, wherein the desired polypeptide excised by ompT protease in the presence of a denaturating agent is refolded by decreasing the concentration of the denaturating agent to obtain an active desired polypeptide.

26. A process according to claim 25, wherein the desired polypeptide is a derivative of *Staphylococcus aureus* having the amino acid sequence of SEQ ID No. 7 from amino acid 125 to amino acid 336 and having protease activity.

27. A process for the production of a desired polypeptide, comprising the steps of:
   (1) transforming *Escherichia coli* host cells with an expression vector comprising a gene coding for a fusion protein comprising at least one protective polypeptide, a desired polypeptide and a linker peptide, wherein the protective polypeptide is a polypeptide derived from *E. coli* β-galactosidase and/or a polypeptide derived from an aminoglycoside 3'-phosphotransferase of transposone 903 origin, the desired polypeptide is a derivative of *Staphylococcus aureus* V8 protease, wherein the derivative has the amino acid sequence of SEQ ID No. 7 from amino acid 125 to amino acid 336 and has protease activity, the linker peptide between said protective polypeptide and said desired polypeptide has a substrate site specifically recognized by a protease intrinsic to the host cells;

(2) expressing said gene in *E. coli* host cells to produce the derivative of the *Staphylococcus aureus* V8 protease as an inactive insoluble fusion protein, which fusion protein forms inclusion bodies wherein said inclusion bodies further comprise *E. coli* ompT protease which is a protease intrinsic to the host cells;

(3) disrupting the cells so as to separate the fusion protein, and obtaining a fraction containing the *E. coli* ompT protease and the fusion protein;

(4) solubilizing the fusion protein with a denaturing agent; and (5) decreasing a concentration of the denaturing agent to a level at which the *E. coli* ompT protease exhibits its activity to cleave the linker peptide with the protease so as to obtain the desired polypeptide from the fusion protein.

28. A process according to claim 27, wherein the denaturing agent for solubilizing the fusion protein is selected from the group consisting of urea, guanidine hydrochloride and a surfactant.

29. A process according to claim 28, wherein a concentration of the urea is 1 to 8 M.

30. A process according to claim 29, wherein a concentration of urea during the cleavage of the fusion protein with the *E. coli* ompT protease is about 4 M.

31. A process according to claim 27, wherein the linker peptide consists of 2 to 50 amino acid residues and contains pairs of two basic amino acids at the N- and C-terminal of the linker peptide or in the linker peptide.

32. A process according to claim 27, wherein the linker peptide has the amino acid sequence RLYRRHHRWGRSG-SPLRAHE (SEQ ID NO: 1).

33. A process according to claim 27, wherein the desired polypeptide is a derivative of the *Staphylococcus aureus* V8 protease having protease activity and having the amino acid sequence selected from the group consisting of SEQ ID NO:5 from amino acid 125 to amino acid 344, SEQ ID NO:6 from amino acid 125 to amino acid 392, SEQ ID NO:22, SEQ ID NO:23, or SEQ ID NO:24.

34. A process according to claim 27, further comprising the step of (6) refolding the desired polypeptide obtained in the step (5) to obtain an active form of the desired polypeptide.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 20 amino acids
      (B) TYPE: amino acid
      (C) STRANDEDNESS: Not Relevant
      (D) TOPOLOGY: linear (ii) MOLECULE TYPE: peptide (xi) SEQUENCE DESCRIPTION: SEQ ID NO:1:

Arg Leu Tyr Arg Arg His His Arg Trp Gly Arg Ser Gly Ser Pro Leu
1               5                   10                  15

Arg Ala His Glu
            20

(2) INFORMATION FOR SEQ ID NO:2:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetic DNA"

(xi) SEQUENCE DESCRIPTION: SEQ ID NO:2:

ACCGCTCGAG GTTATATTAC CAAATAACGA T                                    31

(2) INFORMATION FOR SEQ ID NO:3:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetic DNA"

(xi) SEQUENCE DESCRIPTION: SEQ ID NO:3:

CTTAATGTCG ACTTAAGCTG CATCTGGATT                                      30

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:4:

TCGCGTCGAC TTATTGGTCA TCGTTGGCAA A                             31

(2) INFORMATION FOR SEQ ID NO:5:

(i) SEQUENCE CHARACTERISTICS:
        (A) LENGTH: 344 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

```
Met Thr Met Ile Thr Asp Ser Leu Ala Val Val Leu Gln Arg Arg Asp
  1               5                  10                  15

Trp Glu Asn Pro Gly Val Thr Gln Leu Asn Arg Leu Ala Ala His Pro
             20                  25                  30

Pro Phe Ala Ser Trp Arg Asn Ser Asp Asp Ala Arg Thr Asp Arg Pro
             35                  40                  45

Ser Gln Gln Leu Arg Ser Leu Asn Gly Glu Trp Arg Phe Ala Trp Phe
 50                  55                  60

Pro Ala Pro Glu Ala Val Pro Asp Ser Leu Leu Asp Ser Asp Leu Pro
 65                  70                  75                  80

Glu Ala Asp Thr Val Val Pro Ser Asn Trp Gln Met His Gly Tyr
                     85                  90                  95

Asp Ala Glu Leu Arg Leu Tyr Arg Arg His His Arg Trp Gly Arg Ser
                100                 105                 110

Gly Ser Pro Leu Arg Ala His Glu Gln Phe Leu Glu Val Ile Leu Pro
            115                 120                 125

Asn Asn Asp Arg His Gln Ile Thr Asp Thr Thr Asn Gly His Tyr Ala
130                 135                 140

Pro Val Thr Tyr Ile Gln Val Glu Ala Pro Thr Gly Thr Phe Ile Ala
145                 150                 155                 160

Ser Gly Val Val Val Gly Lys Asp Thr Leu Leu Thr Asn Lys His Val
                165                 170                 175

Val Asp Ala Thr His Gly Asp Pro His Ala Leu Lys Ala Phe Pro Ser
            180                 185                 190

Ala Ile Asn Gln Asp Asn Tyr Pro Asn Gly Gly Phe Thr Ala Glu Asn
            195                 200                 205

Ile Thr Lys Tyr Ser Gly Glu Gly Asp Leu Ala Ile Val Lys Phe Ser
            210                 215                 220

Pro Asn Glu Gln Asn Lys His Ile Gly Glu Val Val Lys Pro Ala Thr
225                 230                 235                 240

Met Ser Asn Asn Ala Glu Thr Gln Val Asn Gln Asn Ile Thr Val Thr
                245                 250                 255

Gly Tyr Pro Gly Asp Lys Pro Val Ala Thr Met Trp Glu Ser Lys Gly
            260                 265                 270
```

```
Lys Ile Thr Tyr Leu Lys Gly Glu Ala Met Gln Tyr Asp Leu Ser Thr
            275                 280                 285

Thr Gly Gly Asn Ser Gly Ser Pro Val Phe Asn Glu Lys Asn Glu Val
        290                 295                 300

Ile Gly Ile His Trp Gly Gly Val Pro Asn Glu Phe Asn Gly Ala Val
305                 310                 315                 320

Phe Ile Asn Glu Asn Val Arg Asn Phe Leu Lys Gln Asn Ile Glu Asp
                325                 330                 335

Ile His Phe Ala Asn Asp Asp Gln
            340

(2) INFORMATION FOR SEQ ID NO:6:

(i) SEQUENCE CHARACTERISTICS:
        (A) LENGTH: 392 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Asp Asp Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Asp Ser Leu Leu Asp Ser Asp Leu Pro
65                  70                  75                  80

Glu Ala Asp Thr Val Val Pro Ser Asn Trp Gln Met His Gly Tyr
                85                  90                  95

Asp Ala Glu Leu Arg Leu Tyr Arg Arg His His Arg Trp Gly Arg Ser
                100                 105                 110

Gly Ser Pro Leu Arg Ala His Glu Gln Phe Leu Glu Val Ile Leu Pro
            115                 120                 125

Asn Asn Asp Arg His Gln Ile Thr Asp Thr Thr Asn Gly His Tyr Ala
130                 135                 140

Pro Val Thr Tyr Ile Gln Val Glu Ala Pro Thr Gly Thr Phe Ile Ala
145                 150                 155                 160

Ser Gly Val Val Val Gly Lys Asp Thr Leu Thr Asn Lys His Val
                165                 170                 175

Val Asp Ala Thr His Gly Asp Pro His Ala Leu Lys Ala Phe Pro Ser
            180                 185                 190

Ala Ile Asn Gln Asp Asn Tyr Pro Asn Gly Gly Phe Thr Ala Glu Asn
        195                 200                 205

Ile Thr Lys Tyr Ser Gly Glu Gly Asp Leu Ala Ile Val Lys Phe Ser
    210                 215                 220

Pro Asn Glu Gln Asn Lys His Ile Gly Glu Val Val Lys Pro Ala Thr
225                 230                 235                 240

Met Ser Asn Asn Ala Glu Thr Gln Val Asn Gln Asn Ile Thr Val Thr
                245                 250                 255

Gly Tyr Pro Gly Asp Lys Pro Val Ala Thr Met Trp Glu Ser Lys Gly
            260                 265                 270
```

```
Lys Ile Thr Tyr Leu Lys Gly Glu Ala Met Gln Tyr Asp Leu Ser Thr
            275                 280                 285

Thr Gly Gly Asn Ser Gly Ser Pro Val Phe Asn Glu Lys Asn Glu Val
        290                 295                 300

Ile Gly Ile His Trp Gly Gly Val Pro Asn Glu Phe Asn Gly Ala Val
305                 310                 315                 320

Phe Ile Asn Glu Asn Val Arg Asn Phe Leu Lys Gln Asn Ile Glu Asp
                325                 330                 335

Ile His Phe Ala Asn Asp Asp Gln Pro Asn Asn Pro Asp Asn Pro Asp
            340                 345                 350

Asn Pro Asn Asn Pro Asp Asn Pro Asn Asn Pro Asp Glu Pro Asn Asn
        355                 360                 365

Pro Asp Asn Pro Asn Asn Pro Asp Asn Pro Asn Gly Asp Asn Asn
370                 375                 380

Asn Ser Asp Asn Pro Asp Ala Ala
385                 390

(2) INFORMATION FOR SEQ ID NO:7:

(i) SEQUENCE CHARACTERISTICS:
        (A) LENGTH: 532 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:7:

Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
                20                  25                  30

Pro Phe Ala Ser Trp Arg Asn Ser Asp Asp Ala Arg Thr Asp Arg Pro
            35                  40                  45

Ser Gln Gln Leu Arg Ser Leu Asn Gly Glu Trp Arg Phe Ala Trp Phe
        50                  55                  60

Pro Ala Pro Glu Ala Val Pro Asp Ser Leu Leu Asp Ser Asp Leu Pro
65                  70                  75                  80

Glu Ala Asp Thr Val Val Val Pro Ser Asn Trp Gln Met His Gly Tyr
                85                  90                  95

Asp Ala Glu Leu Arg Leu Tyr Arg Arg His His Arg Trp Gly Arg Ser
                100                 105                 110

Gly Ser Pro Leu Arg Ala His Glu Gln Phe Leu Glu Val Ile Leu Pro
            115                 120                 125

Asn Asn Asp Arg His Gln Ile Thr Asp Thr Thr Asn Gly His Tyr Ala
        130                 135                 140

Pro Val Thr Tyr Ile Gln Val Glu Ala Pro Thr Gly Thr Phe Ile Ala
145                 150                 155                 160

Ser Gly Val Val Val Gly Lys Asp Thr Leu Thr Asn Lys His Val
                165                 170                 175

Val Asp Ala Thr His Gly Asp Pro His Ala Leu Lys Ala Phe Pro Ser
            180                 185                 190

Ala Ile Asn Gln Asp Asn Tyr Pro Asn Gly Gly Phe Thr Ala Glu Asn
        195                 200                 205

Ile Thr Lys Tyr Ser Gly Glu Gly Asp Leu Ala Ile Val Lys Phe Ser
            210                 215                 220
```

```
Pro Asn Glu Gln Asn Lys His Ile Gly Glu Val Val Lys Pro Ala Thr
225                 230                 235                 240

Met Ser Asn Asn Ala Glu Thr Gln Val Asn Gln Asn Ile Thr Val Thr
                245                 250                 255

Gly Tyr Pro Gly Asp Lys Pro Val Ala Thr Met Trp Glu Ser Lys Gly
            260                 265                 270

Lys Ile Thr Tyr Leu Lys Gly Glu Ala Met Gln Tyr Asp Leu Ser Thr
        275                 280                 285

Thr Gly Gly Asn Ser Gly Ser Pro Val Phe Asn Glu Lys Asn Glu Val
    290                 295                 300

Ile Gly Ile His Trp Gly Gly Val Pro Asn Glu Phe Asn Gly Ala Val
305                 310                 315                 320

Phe Ile Asn Glu Asn Val Arg Asn Phe Leu Lys Gln Asn Ile Glu Asp
                325                 330                 335

Arg Leu Tyr Arg Arg His His Arg Trp Gly Arg Ser Gly Ser Pro Leu
            340                 345                 350

Arg Ala His Glu Gln Phe Leu Glu Cys Gly Asn Gly Lys Thr Ala Phe
        355                 360                 365

Gln Val Leu Glu Glu Tyr Pro Asp Ser Gly Glu Asn Ile Val Asp Ala
    370                 375                 380

Leu Ala Val Phe Leu Arg Arg Leu His Ser Ile Pro Val Cys Asn Cys
385                 390                 395                 400

Pro Phe Asn Ser Asp Arg Val Phe Arg Leu Ala Gln Ala Gln Ser Arg
                405                 410                 415

Met Asn Asn Gly Leu Val Asp Ala Ser Asp Phe Asp Asp Glu Arg Asn
            420                 425                 430

Gly Trp Pro Val Glu Gln Val Trp Lys Glu Met His Lys Leu Leu Pro
        435                 440                 445

Phe Ser Pro Asp Ser Val Val Thr His Gly Asp Phe Ser Leu Asp Asn
    450                 455                 460

Leu Ile Phe Asp Glu Gly Lys Leu Ile Gly Cys Ile Asp Val Gly Arg
465                 470                 475                 480

Val Gly Ile Ala Asp Arg Tyr Gln Asp Leu Ala Ile Leu Trp Asn Cys
                485                 490                 495

Leu Gly Glu Phe Ser Pro Ser Leu Gln Lys Arg Leu Phe Gln Lys Tyr
            500                 505                 510

Gly Ile Asp Asn Pro Asp Met Asn Lys Leu Gln Phe His Leu Met Leu
        515                 520                 525

Asp Glu Phe Phe
530

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:8:

ATCGTTGGCC ATATGGATAT CTTCAATATT                                    30

(2) INFORMATION FOR SEQ ID NO:9:
```

(i) SEQUENCE CHARACTERISTICS:
        (A) LENGTH: 33 base pairs
        (B) TYPE: nucleic acid
        (C) STRANDEDNESS: Not Relevant
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:9:

GACTTATTGG TCATCGAGCT CAAAATGGAT ATC         33

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:10:

GACTTATTGG TCGAGCTCGG CAAAATGGAT         30

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:11:

ATCTGGGTTG AGCTCATCGT TGGCAAAATG GAT         33

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:12:

ATCTGGTTGG AGCTCTTGGT CATCGTTGGC AAA         33

(2) INFORMATION FOR SEQ ID NO:13:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:13:

ACAAAATCAT ATGGAACGCC TATATCGCCG ACAT         34

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:14:

```
AATATTGAAG AGCTCCGCCT ATATCGCCGA CAT                          33
```

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:15:

```
GAATGGCAAA AGCTTATGCA TTTCTTT                                 27
```

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: peptide (v) FRAGMENT TYPE: C-terminal (xi) SEQUENCE DESCRIPTION: SEQ ID NO:16:

```
Asn Ile Glu Asp Arg Leu Tyr Arg Arg His His Arg
1               5                   10
```

(2) INFORMATION FOR SEQ ID NO:17:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: peptide (v) FRAGMENT TYPE: C-terminal (xi) SEQUENCE DESCRIPTION: SEQ ID NO:17:

```
Asn Ile Glu Asp Ile His Met Glu Arg Leu Tyr Arg Arg His His Arg
1               5                   10                  15
```

(2) INFORMATION FOR SEQ ID NO:18:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide (v) FRAGMENT TYPE: C-terminal (xi) SEQUENCE DESCRIPTION: SEQ ID NO:18:

Asn Ile Glu Asp Ile His Phe Glu Leu Arg Leu Tyr Arg Arg His His
1               5                   10                  15
Arg (2) INFORMATION FOR SEQ ID NO:19:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (v) FRAGMENT TYPE: C-terminal (xi) SEQUENCE DESCRIPTION: SEQ ID NO:19:

Asn Ile Glu Asp Ile His Phe Ala Glu Leu Arg Leu Tyr Arg Arg His
1               5                   10                  15
His Arg (2) INFORMATION FOR SEQ ID NO:20:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (v) FRAGMENT TYPE: C-terminal (xi) SEQUENCE DESCRIPTION: SEQ ID NO:20:

Asn Ile Glu Asp Ile His Phe Ala Asn Asp Glu Leu Arg Leu Tyr Arg
1               5                   10                  15
Arg His His Arg
            20

(2) INFORMATION FOR SEQ ID NO:21:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: peptide (v) FRAGMENT TYPE: C-terminal (xi) SEQUENCE DESCRIPTION: SEQ ID NO:21:

Asn Ile Glu Asp Ile His Phe Ala Asn Asp Asp Gln Glu Leu Arg Leu
1               5                   10                  15
Tyr Arg Arg His His Arg
            20

(2) INFORMATION FOR SEQ ID NO:22:

(i) SEQUENCE CHARACTERISTICS:
        (A) LENGTH: 213 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:22:

Val Ile Leu Pro Asn Asn Asp Arg His Gln Ile Thr Asp Thr Thr Asn
1               5                   10                  15

Gly His Tyr Ala Pro Val Thr Tyr Ile Gln Val Glu Ala Pro Thr Gly
                20                  25                  30

Thr Phe Ile Ala Ser Gly Val Val Gly Lys Asp Thr Leu Leu Thr
            35                  40              45

Asn Lys His Val Val Asp Ala Thr His Gly Asp Pro His Ala Leu Lys
        50                  55                  60

Ala Phe Pro Ser Ala Ile Asn Gln Asp Asn Tyr Pro Asn Gly Gly Phe
65                  70                  75                  80

Thr Ala Glu Asn Ile Thr Lys Tyr Ser Gly Glu Gly Asp Leu Ala Ile
                85                  90                  95

Val Lys Phe Ser Pro Asn Glu Gln Asn Lys His Ile Gly Glu Val Val
                100                 105                 110

Lys Pro Ala Thr Met Ser Asn Asn Ala Glu Thr Gln Val Asn Gln Asn
            115                 120                 125

Ile Thr Val Thr Gly Tyr Pro Gly Asp Lys Pro Val Ala Thr Met Trp
130                 135                 140

Glu Ser Lys Gly Lys Ile Thr Tyr Leu Lys Gly Glu Ala Met Gln Tyr
145                 150                 155                 160

Asp Leu Ser Thr Thr Gly Gly Asn Ser Gly Ser Pro Val Phe Asn Glu
                165                 170                 175

Lys Asn Glu Val Ile Gly Ile His Trp Gly Gly Val Pro Asn Glu Phe
                180                 185                 190

Asn Gly Ala Val Phe Ile Asn Glu Asn Val Arg Asn Phe Leu Lys Gln
        195                 200                 205

Asn Ile Glu Asp Ile
        210

(2) INFORMATION FOR SEQ ID NO:23:

(i) SEQUENCE CHARACTERISTICS:
        (A) LENGTH: 214 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:23:

Val Ile Leu Pro Asn Asn Asp Arg His Gln Ile Thr Asp Thr Thr Asn
1               5                   10                  15

Gly His Tyr Ala Pro Val Thr Tyr Ile Gln Val Glu Ala Pro Thr Gly
                20                  25                  30

Thr Phe Ile Ala Ser Gly Val Val Gly Lys Asp Thr Leu Leu Thr
            35                  40              45

Asn Lys His Val Val Asp Ala Thr His Gly Asp Pro His Ala Leu Lys
        50                  55                  60

Ala Phe Pro Ser Ala Ile Asn Gln Asp Asn Tyr Pro Asn Gly Gly Phe
65                  70                  75                  80

Thr Ala Glu Asn Ile Thr Lys Tyr Ser Gly Glu Gly Asp Leu Ala Ile
                85                  90                  95

Val Lys Phe Ser Pro Asn Glu Gln Asn Lys His Ile Gly Glu Val Val
                100                 105                 110

```
Lys Pro Ala Thr Met Ser Asn Asn Ala Glu Thr Gln Val Asn Gln Asn
        115                 120                 125

Ile Thr Val Thr Gly Tyr Pro Gly Asp Lys Pro Val Ala Thr Met Trp
        130                 135                 140

Glu Ser Lys Gly Lys Ile Thr Tyr Leu Lys Gly Glu Ala Met Gln Tyr
145                 150                 155                 160

Asp Leu Ser Thr Thr Gly Gly Asn Ser Gly Ser Pro Val Phe Asn Glu
                165                 170                 175

Lys Asn Glu Val Ile Gly Ile His Trp Gly Gly Val Pro Asn Glu Phe
        180                 185                 190

Asn Gly Ala Val Phe Ile Asn Glu Asn Val Arg Asn Phe Leu Lys Gln
        195                 200                 205

Asn Ile Glu Asp Ile His
        210

(2) INFORMATION FOR SEQ ID NO:24:

(i) SEQUENCE CHARACTERISTICS:
        (A) LENGTH: 215 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:24:

Val Ile Leu Pro Asn Asn Asp Arg His Gln Ile Thr Asp Thr Thr Asn
1               5                   10                  15

Gly His Tyr Ala Pro Val Thr Tyr Ile Gln Val Glu Ala Pro Thr Gly
        20                  25                  30

Thr Phe Ile Ala Ser Gly Val Val Val Gly Lys Asp Thr Leu Leu Thr
        35                  40                  45

Asn Lys His Val Val Asp Ala Thr His Gly Asp Pro His Ala Leu Lys
    50                  55                  60

Ala Phe Pro Ser Ala Ile Asn Gln Asp Asn Tyr Pro Asn Gly Gly Phe
65                  70                  75                  80

Thr Ala Glu Asn Ile Thr Lys Tyr Ser Gly Glu Gly Asp Leu Ala Ile
                85                  90                  95

Val Lys Phe Ser Pro Asn Glu Gln Asn Lys His Ile Gly Glu Val Val
                100                 105                 110

Lys Pro Ala Thr Met Ser Asn Asn Ala Glu Thr Gln Val Asn Gln Asn
        115                 120                 125

Ile Thr Val Thr Gly Tyr Pro Gly Asp Lys Pro Val Ala Thr Met Trp
        130                 135                 140

Glu Ser Lys Gly Lys Ile Thr Tyr Leu Lys Gly Glu Ala Met Gln Tyr
145                 150                 155                 160

Asp Leu Ser Thr Thr Gly Gly Asn Ser Gly Ser Pro Val Phe Asn Glu
                165                 170                 175

Lys Asn Glu Val Ile Gly Ile His Trp Gly Gly Val Pro Asn Glu Phe
        180                 185                 190

Asn Gly Ala Val Phe Ile Asn Glu Asn Val Arg Asn Phe Leu Lys Gln
        195                 200                 205

Asn Ile Glu Asp Ile His Phe
        210                 215
```